United States Patent
Slama-Schwok et al.

(10) Patent No.: US 9,409,937 B2
(45) Date of Patent: Aug. 9, 2016

(54) FAMILY OF ANALOGUES AND NADP+ OR NADPH, THEIR PREPARATION AND THEIR APPLICATION IN THERAPEUTICS

(75) Inventors: Anny Slama-Schwok, St Aubin (FR); Jean-Luc Boucher, Fontenay sous Bois (FR); Yun Xu-Li, Paris (FR); Eric Deprez, Boissette (FR); Etienne Henry, Motrouge (FR); Chantal Dessy, Wezembeek-Oppem (BE); Olivier Feron, Wezembeek-Oppem (BE); Bogdan Tarus, Montighy les Metz (FR)

(73) Assignee: UNIVERSITE PARIS DESCARTES, Paris (FR)

( * ) Notice: Subject to any disclaimer, the term of this patent is extended or adjusted under 35 U.S.C. 154(b) by 58 days.

(21) Appl. No.: 14/128,161

(22) PCT Filed: Jun. 19, 2012

(86) PCT No.: PCT/EP2012/061744
§ 371 (c)(1),
(2), (4) Date: Mar. 24, 2014

(87) PCT Pub. No.: WO2012/175516
PCT Pub. Date: Dec. 27, 2012

(65) Prior Publication Data
US 2014/0193339 A1    Jul. 10, 2014

(30) Foreign Application Priority Data
Jun. 21, 2011   (EP) .................................. 11305779

(51) Int. Cl.
*A61K 49/00* (2006.01)
*C07F 9/6561* (2006.01)
*C07H 19/16* (2006.01)
*C07H 19/167* (2006.01)

(52) U.S. Cl.
CPC ............. *C07F 9/65616* (2013.01); *A61K 49/00* (2013.01); *C07H 19/16* (2013.01); *C07H 19/167* (2013.01)

(58) Field of Classification Search
CPC .............................. A61K 49/00; C07D 473/34
USPC ........................................................ 424/9.1
See application file for complete search history.

(56) References Cited

FOREIGN PATENT DOCUMENTS

| FR | 2 893 617 A1 | 5/2007 | |
|---|---|---|---|
| FR | 2893617 A1 | * 5/2007 | ........... C07D 473/34 |

OTHER PUBLICATIONS

European Search Report, dated Oct. 10, 2011, from corresponding European application.
International Search Report, dated Aug. 1, 2012, from corresponding PCT application.
Edward Beaumont et al., "Synchronous Photoinitiation of Endothelial NO Synthase Activity by a Nanotrigger Targeted at Its NADPH Site", Journal of the American Chemical Society, Feb. 1, 2007, pp. 2178-2186, vol. 129, No. 7.
Edward Beaumont et al., "NO Formation by Neuronal No-Synthase can be Controlled by Ultrafast Electron Injection from a Nanotrigger", Chembiochem, Mar. 2, 2009, pp. 690-701, vol. 10, No. 4.
Jean-Christophe Lambry et al., "Selective probing of a NADPH site controlled light-induced enzymatic catalysis", Journal of Molecular Recognition, Jul. 1, 2010, pp. 379-388, vol. 23, No. 4.

* cited by examiner

*Primary Examiner* — Michael G Hartley
*Assistant Examiner* — Jagadishwar Samala
(74) *Attorney, Agent, or Firm* — Young & Thompson

(57) ABSTRACT

A new family of analogues of NADP+ or NADPH, their preparation and their application in therapeutics.

10 Claims, 11 Drawing Sheets

A

B

YL3 (0 µM)  YL3 (1µM)  YL3 (5µM)

Figure 1A:
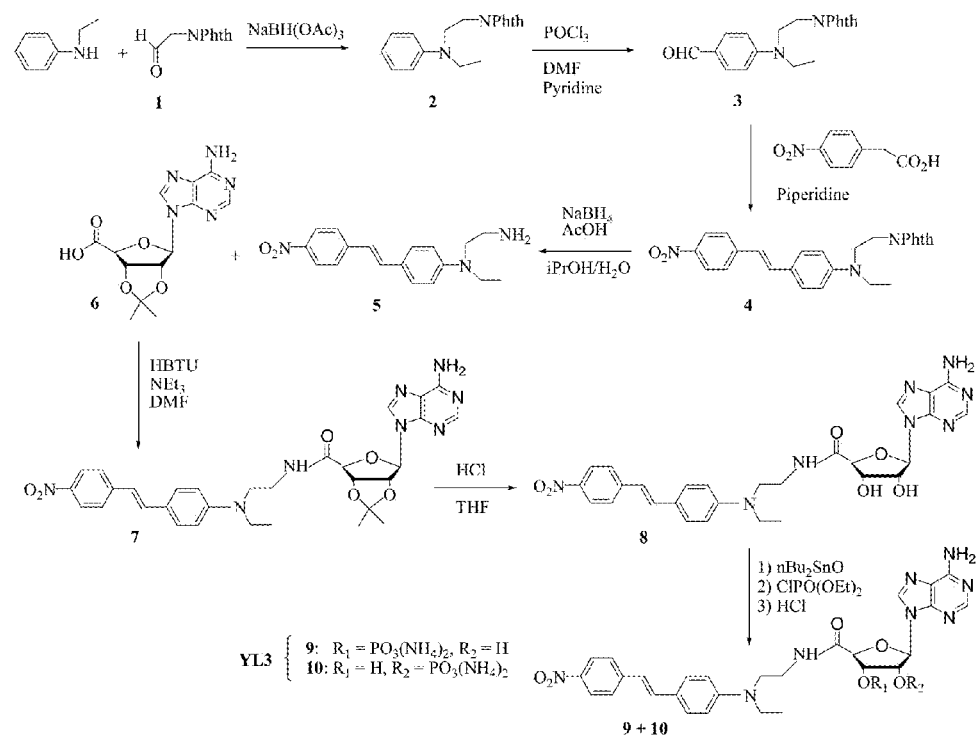

FAMILY OF ANALOGUES AND NADP+ OR NADPH, THEIR PREPARATION AND THEIR APPLICATION IN THERAPEUTICS

The present invention concerns a new family of analogues of NADP+ or NADPH, their preparation and their application in therapeutics.

Blood supply is essential to most solid tumors since nutrients are brought by blood vessels developed around and inside the tumors. The formation of neo-vasculature by angiogenesis is necessary for solid tumor progression and metastasis. However, tumor blood vessels differ in their morphology from their normal counterparts. In particular, tumor vasculature usually fails to meet the demands of the tumor cells for oxygen and nutrients; this failure results in tumor blood flow heterogeneity often inducing intermittent hypoxia, and acidic conditions within the tumor (Ingram et Porter, *Gene Ther* 2005, 12, 1058-69).

Hypoxia often found in solid tumors induces the hypoxia-inducible factor HIF-1α, in turn promoting VEGF-associated angiogenesis (VEGF: Vascular Endothelial Growth Factor). HIF-1α acts as an oxygen sensor forming together with the associated $O_2$-dependent HIF-prolyl hydroxylase an auto-regulating loop (Berchner-Pfannschnidt et al., *J Biol Chem* 2007, 282, 1788-96).

The recognition of the vascular bed as an important target leads to the development of the anti-angiogenesis strategy that prevents the formation of new blood vessels and normalizes the remaining vessels. In the context of anti-angiogenic therapies, some anti-angiogenic agents have been developed to target VEGF, one of the main proteins involved in neovascularization. These anti-antiogenic agents are, for example, anti-VEGF antibodies, VEGF receptors inhibitors or VEGFR kinase inhibitors.

However, it was observed that these compounds could not target tumors efficiently without being co-delivered with a "vehicle" (Chen et al., *J Biol Chem* 2010, 285, 22639-50). Such "vehicle" for tumor targeting of a pharmaceutical compound could be fluorescent or magnetic nanoparticles, which have often considerable side effect because of their toxicity, short half-life time, or poor bioavailability Specific antibodies which recognize some over-expressed receptors in a tumor can also be used for delivery of a gene or a siRNA in gene therapy. However, since tumors could not always be well vascularized, nucleic acids fragments often could not well penetrate into cells located at the core of a solid tumor.

Since the inhibition of VEGF activity is not always beneficial to tumor inhibition, and anti-angiogenic agents targeting VEGF could not always be efficaciously delivered into tumors, it is necessary to develop new anti-angiogenic compounds targeting other proteins involved in tumor vascularization.

In mammals, nitric oxide (NO) is an endogenously produced free radical. It is involved in many (patho)physiological processes in the cardiovascular, nervous and immune systems. It displays both anti-viral and anti-bacterial properties and exerts important roles in apoptosis. NO can also promote vasodilation of blood vessel. NO modulates oxygen-sensing by HIF-1α under hypoxia but S-nitrosylation stabilizes HIF-la under normoxia (Sonveaux et al., *Int J radiat Oncol Biol Phys* 2007, 67, 1155-62).

NO is synthesized by heme-proteins called NO synthases (NOS) that oxidize L-arginine to NO. There are three isoforms of NO-synthases in mammal: neuronal NOS (nNOS or NOS-1), inducible NOS (iNOS or NOS-2) and endothelial NOS (eNOS or NOS-3). The main source of NO in the vasculature is eNOS.

Although two conflicting views relating to the role of NO in carcinogenesis and tumor progression exist, recent studies show that there is a positive correlation between the expression of iNOS or eNOS and progression of several human cancers (Muntane et IaMata, *World J. Hepatol* 2010, 2, 337-344; Jadeski et al., *Int. J. Cancer* 2003, 106, 496-504).

The inhibition of NO synthases provides another anti-angiogenesis therapeutic approach which is different from herein before mentioned conventional anti-angiogenic agents targeting VEGF proteins.

Many NO synthases inhibitors are already known in the prior art, such as analogues of substrate L-arginine, analogues of cofactor tetrahydrobiopterine, heme ligands, or dimerisation inhibitors. However, most of NO synthases inhibitors described in the literature could not specifically inhibit one isoform of NO synthase, in particular eNOS. In fact, these inhibitors all target the oxygenase domain of NO synthases. The great similarity among the oxygenase domains in different NO-synthases isoforms makes it difficult to specifically inhibit one iso form without inhibition of another isoform.

The French patent application FR 2 893 617 discloses photoactivable analogues of NADPH or NADP+, NAD, NAD+, NADH. The compounds disclosed in FR 2 893 617 are able to initiate the enzymatic catalysis of NADPH or NADP+, NAD, NAD+, NADH dependent-enzymes and are useful to study the mechanism of said enzymes. However, said compounds can not inhibit NADPH dependant enzymes activity.

The present invention provides new compounds which could inhibit the activity of NADP+-, or NADPH-dependent enzymes, in particular eNOS.

The present invention also provides new compounds which could be used as anti-tumoral drugs.

The present invention also provides new compounds which could be useful for in vitro cancer diagnosis.

The present invention relates to compounds of formula (I):

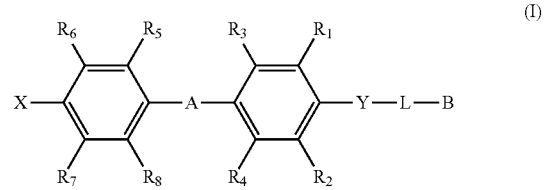

wherein:
(i) X represents an electron acceptor group, chosen from the group comprising:
—$NO_2$,
—CN,
—CHO,
—COOH,
—$CF_3$,
—F,
—CH=$C(CN)_2$,
—$SO_3H$,
$CONR_9R_{10}$ or $SO_2NR_9R_{10}$, in which $R_9$ and $R_{10}$ represent each independently of each other an hydrogen, a linear or branched ($C_1$-$C_3$) alkyl group, or an aryl group,
$COR_9$, in which $R_9$ represents an hydrogen, a linear or branched ($C_1$-$C_3$) alkyl group, or an aryl group, or a tetrazolyl group, (ii) Y represents an electron donor group, chosen from the group comprising —NR$_{19}$—, —OC(R$_{19}$R$_{14}$)—, or —SC(R$_{19}$R$_{14}$)—, in which:
R$_{19}$ is chosen from:
  a hydrogen,
  a linear (C$_1$-C$_8$) alkyl group, in particular an ethyl, said alkyl group being optionally substituted by one or more group selected from: —OH group, —NH$_2$ group, —COOH group, CONH-aryl-COOH group or NHCO-arylCOOH group or NHCOarylsulfate group, or NHCOarylsulfonate group, wherein the aryl group is chosen from phenyl, naphtyl or biphenyl,
  a hydrosoluble organic group, in particular PEG,
R$_{14}$ represents a hydrogen or a linear or branched (C$_1$-C$_4$) alkyl group, optionally substituted by —OH.
(iii) A represents a bond chosen from the group comprising:
  (a) —C≡C—, or

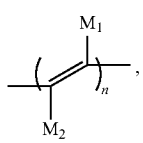
(b)

wherein:
  M$_1$ and M$_2$ represent independently of each other H, F, Cl, Br or I,
  n is an integer chosen from 1, 2, or 3,
(iv) R$_1$, R$_2$, R$_3$, R$_4$, R$_5$, R$_6$, R$_7$ or R$_8$ are each independently selected from the group comprising:
  H,
  F, Cl, Br, I,
  a linear or branched (C$_1$-C$_4$) alkyl, optionally substituted by one or more substituents chosen from:
    OH,
    —NR$_{11}$R$_{12}$, in which R$_{11}$ and R$_{12}$ represent each independently of each other an hydrogen or a linear or branched (C$_1$-C$_3$) alkyl group, or
    COOR$_{11}$, in which R$_{11}$ represents hydrogen or a linear or branched (C$_1$-C$_3$) alkyl group,
  CONHR$_{13}$ or NHCOR$_{13}$, in which R$_{13}$ represents a linear or branched (C$_1$-C$_4$) alkyl group,
(v) L represents a spacer group selected from the group comprising:

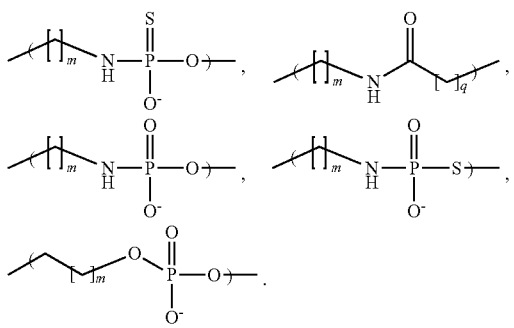

wherein m and q represent each independently of each other an integer chosen from 0 to 5, said groups being optionally substituted by one or more OH, (vi) B represents the following formula II:

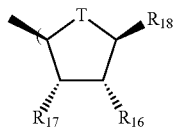

wherein:
  T represents an oxygen atom, or a sulphur atom, preferably an oxygen atom;
  R$_{16}$ and R$_{17}$ represent each independently of each other OH, H$_2$PO$_4$, HSO$_4$, OPO$_3$(NH$_4$)$_2$, or any salt of these phosphate or sulphate groups,
  R$_{18}$ represents a purine-base or a pyrimidine-base, in particular adenine, guanine, hypoxanthine, thymine, uracil or cytosine, preferably adenine, under racemate or isomeric forms, in particular axial or equatorial isomeric forms, and pharmaceutically acceptable salts thereof.

The term "alkyl" refers to a linear or branched chain, saturated hydrocarbon having the indicated number of carbon atoms. A (C$_1$-C$_3$) alkyl is meant to include but is not limited to methyl, ethyl, propyl, isopropyl. An alkyl group can be unsubstituted or optionally substituted with one or more substituents. A (C$_1$-C$_4$) alkyl group further comprises n-butyl, isobutyl, sec-butyl, tert-butyl. A (C$_1$-C$_8$) alkyl group further comprises n-pentyl, isopentyl, n-hexyl, n-heptyl, n-octyl.

Without other specification, the term "aryl" refers to an unsubstituted aromatic system, such as a phenyl, or substituted aromatic system by at least one OH group, at least one (C$_1$-C$_3$) alkyl group, or at least one (C$_1$-C$_3$) alkoxy group. An alkoxy group is meant to include but is not limited to methoxy, ethoxy, propoxy.

The term "tetrazolyl group" refers to a heterocyclic group, having five atoms ring consisting of four nitrogen and a carbon atom, said ring being unsubstituted or optionally substituted by at least one of a OH group, a (C$_1$-C$_3$) alkyl group, or a C$_1$-C$_3$ alkoxy group, as defined above.

The term "electron acceptor" means a chemical entity that accepts electrons transferred to it from another compound. In the context of a push-pull compound, an electron acceptor group withdraws electronic density to the conjugated linker.

The term "electron donor" means a chemical entity that donates electrons to another compound. In the context of a push-pull compound, an electron donor group adds electronic density to the conjugated linker.

A push-pull compound is a compound constituted of a donor group at one side and an acceptor group at the other side.

According to the present invention, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts.

The present invention is based on the inhibitory effect of the compounds of the formula (I) on the enzymatic activity of nNOS, a NADPH dependent-enzyme; the inhibitory effect originates from its competition with NADPH binding.

For the first time, the Inventors of the present invention provide an inhibitor of NADPH dependent enzymes, which targets the reductase domain of NADPH dependent-enzymes, for example nitric oxide synthase, quinone oxido-reductases, and NADPH oxidases.

The radicals $R_1, R_2, R_3, R_4, R_5, R_6, R_7$ or $R_8$ confer different electronic and binding properties to the compound of formula (I).

The radical $R_{19}$ confers to the compound of formula (I) a better interaction with variable residues in reductase domain of NADPH dependent-enzymes, thus conferring specificity.

The length of the bond A between the two aryl groups determines the total length of the compounds of the invention. Increasing the number of C—C double bonds between the two aryl groups can shift the maximum absorption to higher wavelengths, and increases significantly the two photo absorption cross-sections in the red-NIR region. However, the total length of the compounds of formula (I) must be controlled for efficient enzymatic site binding. If the double bond length is too important, then the compound does not fit within the active site of the enzyme.

In one embodiment, the present invention relates to compounds of formula (I) wherein X represents CN and A represents

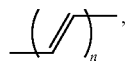

n being an integer chosen from 1 to 3, $R_1, R_2, R_3, R_4, R_5, R_6, R_7$ or $R_8$ are each independently selected from the group comprising:

H, F, Cl, Br, I, a branched ($C_1$-$C_4$) alkyl, optionally substituted by one or more substituants chosen from:

OH,

—$NR_{11}R_{12}$, in which $R_{11}$ and $R_{12}$ represent each independently of each other an hydrogen or a linear or branched ($C_1$-$C_3$) alkyl group, or $COOR_{11}$, in which $R_{11}$ represents hydrogen or a linear or branched ($C_1$-$C_3$) alkyl group, $CONHR_{13}$ or $NHCOR_{13}$, in which $R_{13}$ represents a linear or branched ($C_1$-$C_4$) alkyl group.

Y is as defined herein before.

In a particular embodiment, the present invention provides compounds of formula (I), wherein:

X represents an electron acceptor group, chosen from the group comprising:

—$NO_2$,

—CN,

—CHO,

—COOH,

—$CF_3$,

—F,

—CH=C(CN)$_2$,

—$SO_3H$, $CONR_9R_{10}$ or $SO_2NR_9R_{10}$, in which $R_9$ and $R_{10}$ represent each independently of each other an hydrogen, a linear or branched ($C_1$-$C_3$) alkyl group, or an aryl group, $COR_9$, in which $R_9$ represents an hydrogen, a linear or branched ($C_1$-$C_3$) alkyl group, or an aryl group, or a tetrazolyl group, Y represents —$NR_{19}$—, $R_1, R_2, R_3, R_4, R_5, R_6, R_7, R_8, L, R_{18}, R_{16}, R_{17}$ and $R_{19}$ are as defined herein before, said compounds responding to the following formula (Ia):

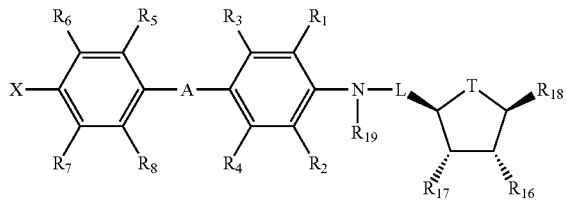

In a more particular embodiment, the present invention provides compounds of formula (Ia), wherein:
T represents an oxygen atom,
$R_{18}$ represents an adenine group,
$R_1, R_2, R_3, R_4, R_5, R_6, R_7, R_8, X, L, R_{16}, R_{17}$ and $R_{19}$ are as defined herein before,
L represents

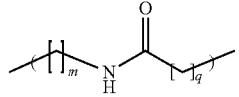

wherein m represents an integer chosen from 0 to 5, q represents 0, said compounds responding to following formula (Ii):

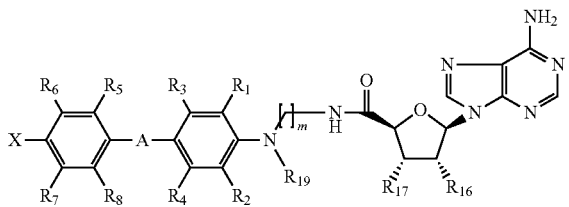

In a more particular embodiment, the present invention provides compounds of formula (Ia), wherein:
A represents:

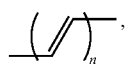

n being an integer chosen from 1, 2 or 3,
T represents an oxygen atom,
$R_{18}$ represents an adenine group,
$R_1, R_2, R_3, R_4, R_5, R_6, R_7, R_8, X, L, R_{16}, R_{17}$ and $R_{19}$ are as defined herein before, said compounds responding to following formula (Ib):

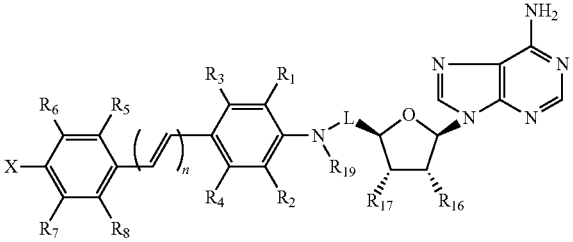

In a more particular embodiment, the present invention provides compounds of formula (Ib), wherein:
L represents

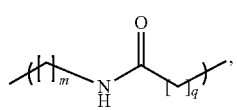

wherein m represents an integer chosen from 0 to 5, q represents 0,

X, n, $R_1$, $R_2$, $R_3$, $R_4$, $R_5$, $R_6$, $R_7$, $R_8$, $R_{16}$, $R_{17}$ and $R_{19}$ are as defined herein before, said compounds responding to following formula (Ic):

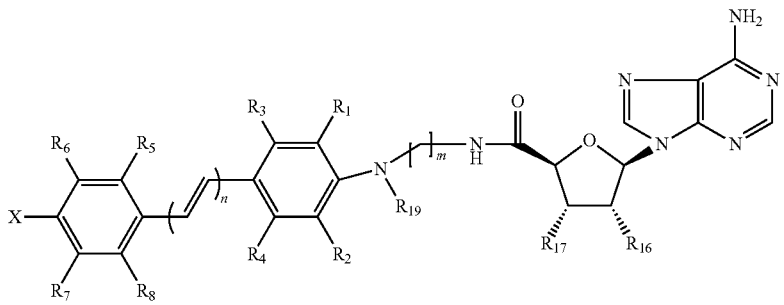

In a still more particular embodiment, the present invention provides compounds of formula (Ic), wherein:
$R_1$, $R_2$, $R_3$, $R_4$, $R_5$, $R_6$, $R_7$, $R_8$ respectively represents a hydrogen atom,
$R_{19}$ represents an ethyl group,
$R_{16}$, $R_{17}$, X are as defined herein before,
n represents an integer chosen from 1, 2 or 3,
m represents an integer chosen from 0 to 5,
said compounds responding to following formula (Id):

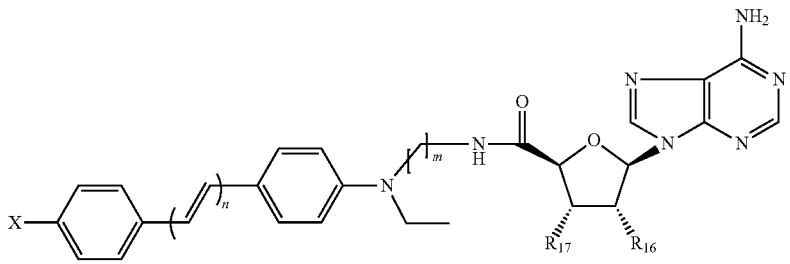

In a favourable embodiment, the present invention provides compounds of formula (Id), wherein:
m represents the integer 2,
$R_{16}$, $R_{17}$, X are as defined herein before,
n represents 1, 2 or 3, said compounds responding to following formula (Ie)

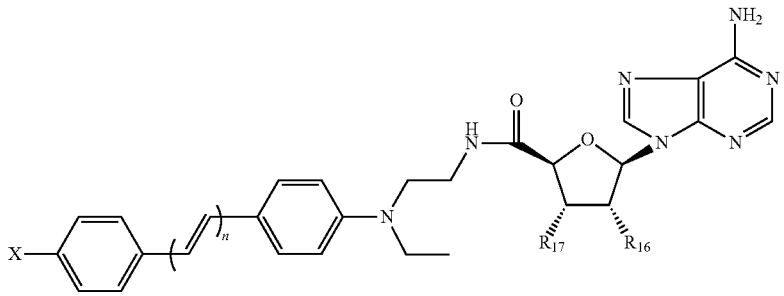

In another favourable embodiment, the present invention provides compounds of formula (Id), wherein:
n represents the integer 1,
$R_{16}$, $R_{17}$, X are as defined herein before,
m represents an integer chosen from 0 to 5, said compounds responding to following formula (If):

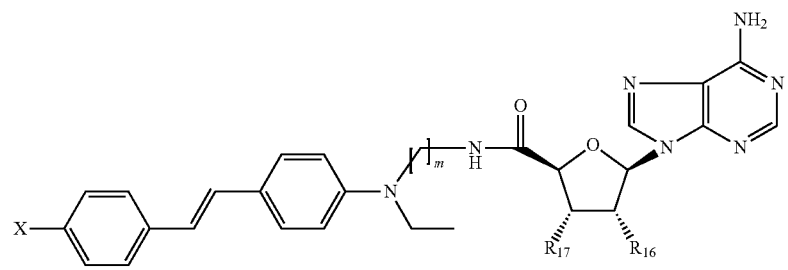

In another favourable embodiment, the present invention provides compounds of formula (Id), wherein:
X represents —$NO_2$ or CN group,
$R_{16}$, $R_{17}$ are as defined herein before,
n represents an integer selected from 1, 2 or 3,
m represents an integer chosen from 0 to 5, said compounds responding to following formula ($Ig_1$):

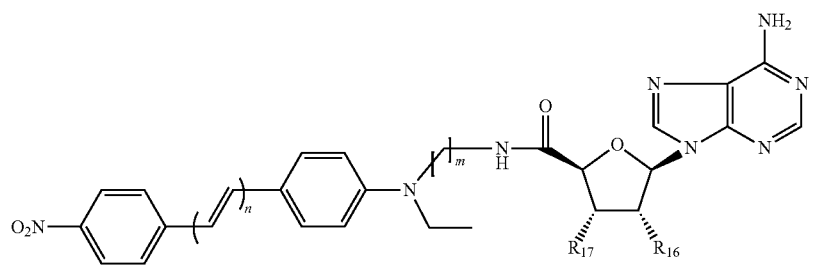

or following formula ($Ig_2$):

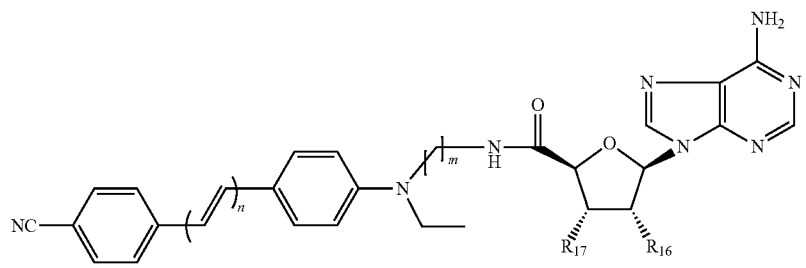

In a more favourable embodiment, the present invention provides compounds of formula (Ig$_1$), wherein:
n represents integer 1,
m represents integer 2,
R$_{16}$, R$_{17}$ represent each independently of each other OH, H$_2$PO$_4$, HSO$_4$, OPO$_3$(NH$_4$)$_2$, or any salt of these phosphate or sulphate groups,
said compounds responding to following formula (Ih$_1$):

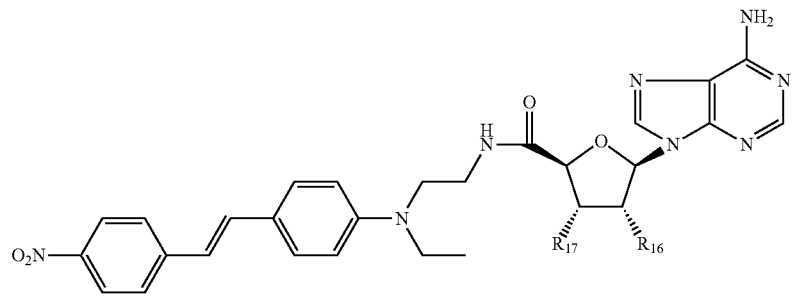

In a more favourable embodiment, the present invention provides compounds of formula (Ig$_2$), wherein:
n represents integer 1,
m represents integer 2,
R$_{16}$, R$_{17}$ represent each independently of each other OH, H$_2$PO$_4$, HSO$_4$, OPO$_3$(NH$_4$)$_2$, or any salt of these phosphate or sulphate groups,
said compounds responding to following formula (Ih$_2$):

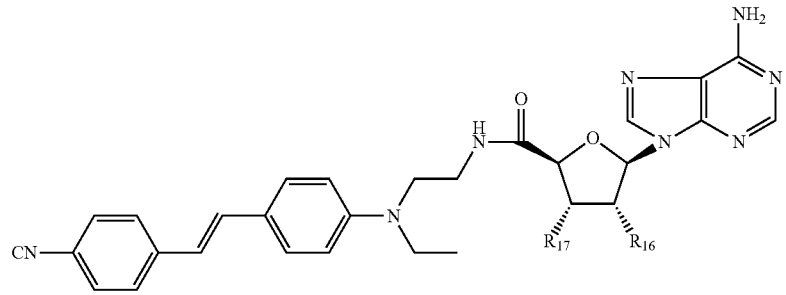

In a particularly favourable embodiment, the compounds of the represent invention of formula (Ia) are selected from the group comprising:

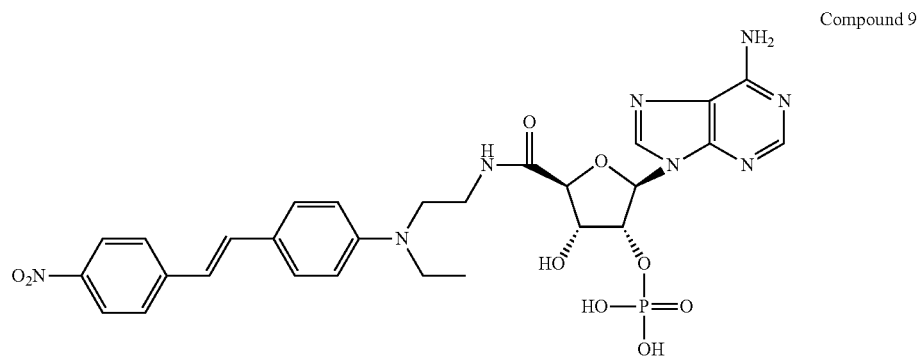

Compound 9

-continued
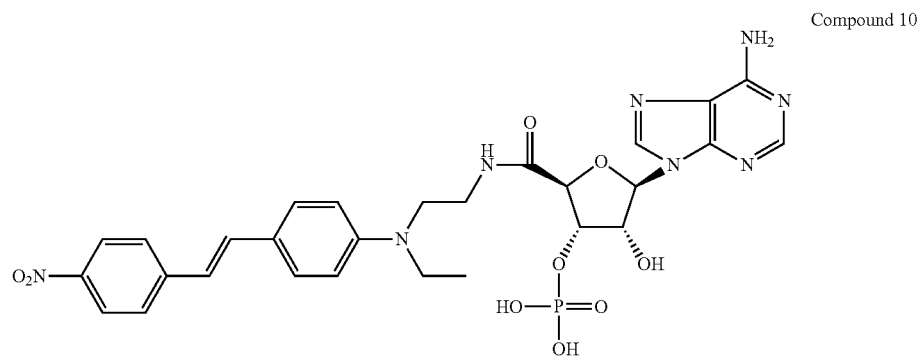
Compound 10
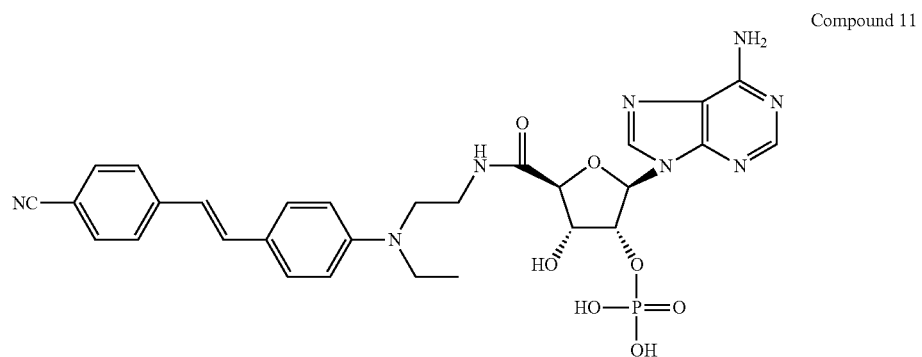
Compound 11
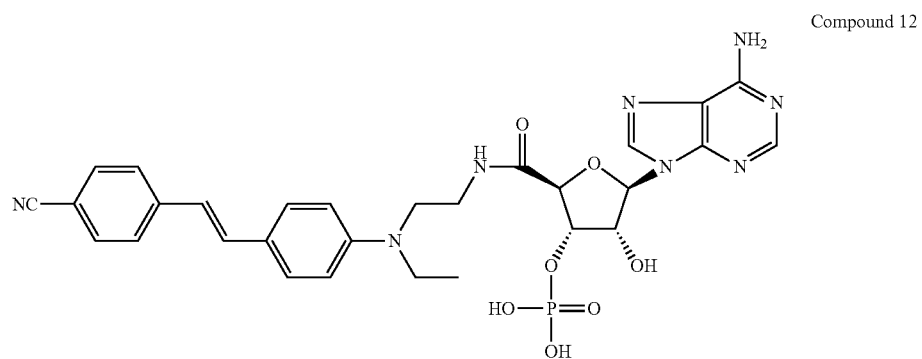
Compound 12
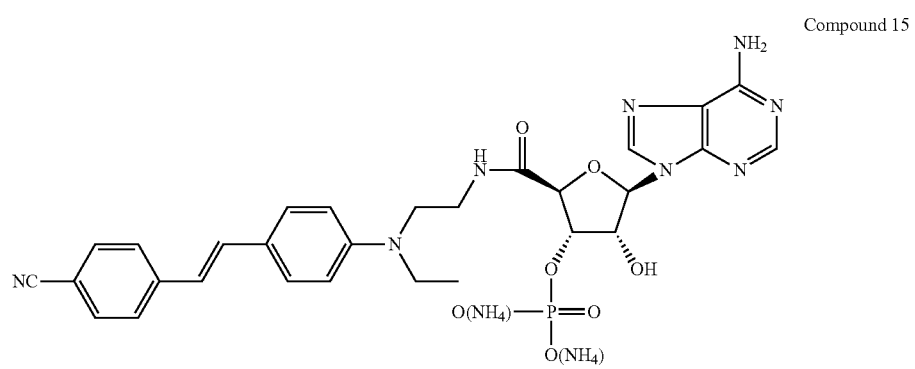
Compound 15

-continued

Compound 16

Compounds according to the invention can be prepared according to methods well known for one skilled in the art which are described in the literature.

The present invention provides also a method for preparing a compound of formula (Ia) comprising:
(i) preparing a compound of formula III Formula (III)

wherein:
X represents an electron acceptor group, chosen from the group comprising:
—$NO_2$,
—CN,
—CHO,
—COOH,
—$CF_3$,
—F,
—CH═C(CN)$_2$,
—$SO_3H$,
CONR$_9$R$_{10}$ or SO$_2$NR$_9$R$_{10}$, in which R$_9$ and R$_{10}$ represent each independently of each other an hydrogen, a linear or branched (C$_1$-C$_3$) alkyl group, or an aryl group,
COR$_9$, in which R$_9$ represents an hydrogen, a linear or branched (C$_1$-C$_3$) alkyl group, or an aryl group, or
a tetrazolyl group,
A represents a bond chosen from the group comprising:
(a) —C≡C—, or (b)

wherein:
$M_1$ and $M_2$ represent independently of each other H, F, Cl, Br or I,
n is an integer chosen from 1, 2, or 3, $R_1$, $R_2$, $R_3$, $R_4$, $R_5$, $R_6$, $R_7$ or $R_8$ are each independently selected from the group comprising:
H,
F, Cl, Br, I,
a linear or branched (C$_1$-C$_4$) alkyl, optionally substituted by one or more substituents chosen from:
OH,
—NR$_{11}$R$_{12}$, in which R$_{11}$ and R$_{12}$ represent each independently of each other an hydrogen or a linear or branched (C$_1$-C$_3$) alkyl group, or
COOR$_{11}$, in which R$_{11}$ represents hydrogen or a linear or branched (C$_1$-C$_3$) alkyl group,
CONHR$_{13}$ or NH CO R$_{13}$, in which R$_{13}$ represents a linear or branched (C$_1$-C$_4$) alkyl group,
E represents —NR$_{19}$R$_{15}$, wherein:
R$_{19}$ is chosen from:
a hydrogen,
a linear (C$_1$-C$_8$) alkyl group, in particular an ethyl, said alkyl group being optionally substituted by one or more group selected from: —OH group, —NH$_2$ group, —COOH group, CONH-arylCOOH (aryl=phenyl, naphtyl, biphenyl), NHCOaryl-COOH, NHCOarylOSO$_3$H, or NHCOarylSO$_3$H,
a hydrosoluble organic group, in particular PEG,
R$_{15}$ represents —(CH$_2$)$_t$—NHZ, wherein t is an integer chosen from 1 to 5, and Z represents a protecting group chosen from the group comprising phthaloyl (phth), tert-butyloxycarbonyl (Boc), benzyl (Bn),
(ii) reacting said compound of formula III with a compound of formula II(a)

Formula (IIa)

wherein:
$Z_1$ and $Z_2$ represent alcohol protecting group chosen from benzyl, benzoyl, silyl ether like TMS (trimethylsilyl) or OZ$_1$ and OZ$_2$ forming together an isopropylidene group,
R$_{18}$ represents a purine-base or a pyrimidine-base, in particular adenine, guanine, hypoxanthine, thymine, uracil or cytosine, preferably adenine, to obtain a compound which is deprotected to yield compounds of formula (Ia), wherein $R_{16}$ and $R_{17}$ are OH.

Said compound being treated with a phosphate or a sulphate derivative to yield compound of the invention, wherein $R_{16}$ or $R_{17}$ is $H_2PO_4$, $HSO_4$ or $OPO_3(NH_4)_2$.

The reaction in step (ii) can be carried out, for example, in anhydrous DMF (dimethylformamide) in presence of HBTU (1H-benzotriazol-1-yl)-1,1,3,3-tetramethyluronium hexafluorophosphate).

The compound of formula III is a chromophore having an absorption maximum at a wavelength found in the range 300 and 700 nm with a molar extinction coefficient higher than 10 000$M^{-1} \cdot cm^{-1}$ and it can emit fluorescence under a two photon excitation at a wavelength between 700 et 1100 nm, with a two-photon cross section $\sigma_2$ larger than 30 GM, preferentially larger than 100 GM.

As for example, a mixture of compounds 9 and 10 may be synthesized according to the scheme represented in FIG. 1A.

When A represents

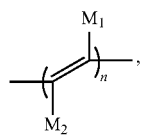

if n=1, then the compound of formula I may be considered as a stillbene derivative, wherein the double bond between the two phenyl group can be either in cis form or in trans form. The compounds of cis form are not active, since they are unable to bind eNOS and do not inhibit eNOS activity, while compounds of trans form are active and can efficiently inhibit eNOS activity; if n=2 or 3, then compound of the present invention is active, while all of the double bonds in A are trans form.

Interestingly, since they are not active under the cis form, they are devoid of secondary effects and they can be administrated under inactive form and transformed into the active form directly in situ after irradiation.

Under laser irradiation at a wavelength between 300 and 700 nm, the compounds of the present invention prepared as a mixture of cis and trans isomers or as pure cis isomer can be transformed to the active trans form following two photons excitation. This cis-trans mixture could be obtained following a distinct synthesis route involving Wittig coupling as the key step. Molecular modeling shows that the cis isomer can not bind to the NADPH site and is inactive.

As an example, the following scheme represents the transformation of cis isomer of compound A to trans isomer under visible light irradiation.

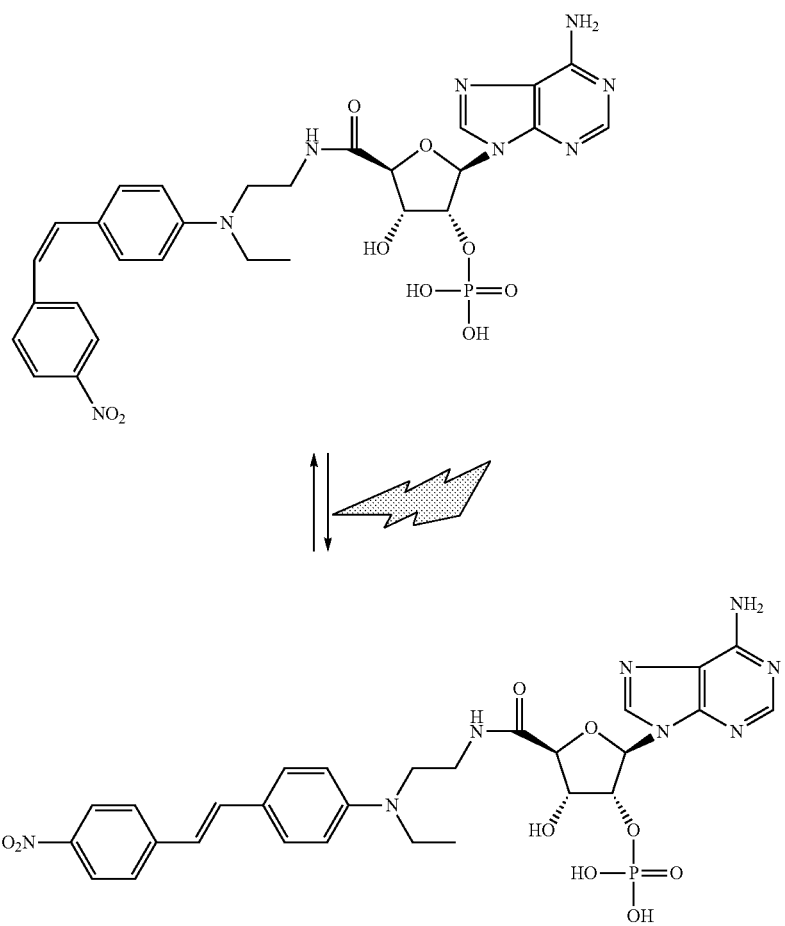

In an embodiment, the present invention provides the aforementioned compounds of formula (I) in trans form, wherein the bond A between two aryls of the aforementioned compounds is represented by

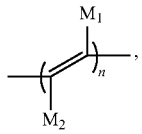

wherein $M_1$ and $M_2$ represent independently of each other H, F, Cl, Br or I.

In a particular embodiment, the present invention provides the aforementioned compounds of formula (I), (Ia), (Ii), when the bond between two aryls of the aforementioned compounds is a double bond, (Ib), (Ic), (Id), (Ie), (If), (Ig$_1$), (Ig$_2$), (Ih$_1$), (Ih$_2$) and compounds 9, 10, 11, 12, 15 or 16 in biological active trans form.

In another embodiment, the present invention provides the aforementioned compounds of formula (I) in cis form, wherein the bond A between two aryls of the aforementioned compounds is represented by

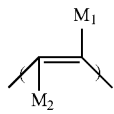

wherein $M_1$ and $M_2$ represent independently of each other H, F, Cl, Br or I.

In a particular embodiment, the present invention provides the aforementioned compounds of formula (I), (Ia), (Ii), when the bond between two aryls of the aforementioned compounds is a double bond, (Ib), (Ic), (Id), (Ie), (If), (Ig$_1$), (Ig$_2$), (Ih$_1$), (Ih$_2$) and compounds 9, 10, 11, 12, 15 or 16 in cis form.

The present invention still provides compounds of formula (I) as a drug for its use in chemotherapy.

In an embodiment, the present invention provides for the use of a compound of formula (I) as an anti-angiogenic agent in chemotherapy for treating cancers, particularly for treating superficial cancers, such as melanomas, upper respiratory tract cancers, or upper aerodigestive tract cancers.

The present invention provides also photoactivable compounds of formula (I), wherein the bond A between two aryls of the aforementioned compounds is a double bond.

In an embodiment, the present invention provides for use of a compound of formula (I) as an imaging agent in cancer diagnostic, particularly in superficial cancer diagnostic.

The present invention provides also photoactivable composition comprising at least a compound of formula (I), wherein the bond A is represented by

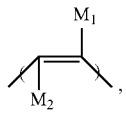

and is under cis form, or bond A is under both cis and trans form, wherein $M_1$ and $M_2$ represent independently of each other H, F, Cl, Br or I.

In accordance with this invention, the compounds of formula (I) or their pharmaceutically acceptable salts are useful in pharmaceutically acceptable compositions. The pharmaceutical compositions according to the invention comprise as active ingredient one or more of the compounds of formula (I) or its pharmaceutically acceptable salts, in combination with excipients and/or pharmaceutically acceptable diluents or carriers. Any conventional carrier material can be utilized. The carrier material can be an organic or inorganic inert carrier material, for example one that is suitable for oral administration or in situ injection. Suitable carriers include water, gelatin, arabic gum, lactose, starch, magnesium stearate, talc, vegetable oils, polyalkylene-glycols, glycerine and petroleum jelly. Additional additives such as flavoring agents, preservatives, stabilizers, emulsifying agents, buffers and the like may be added in accordance with accepted practices of pharmaceutical compounding.

The pharmaceutical preparations can be made up in any conventional form including a solid form for oral administration such as tablets, capsules, pills, powders, granules, and rectal suppositories. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes.

Furthermore, the pharmaceutical preparations may also contain one compound of formula (I), in particular of formula (Ia), and other anti-cancer agents, chosen from the group comprising:
an anti-angiogenic agent, selected from Cilengitide, Vandetanib, Lenalidomide, Thalidomide, Arsenic Trioxide, Bevacizumab, anti-VEGFR-1, anti-VEGFR-2, anti-PDGFR, anti-FMS-FLT-3, anti-TK1,
alkylating agents, selected from Bendamustine, Temozolomide, Mechlorethamine, Cyclophosphamide, Carmustine, Cisplatine, Busulfan, Thiotepa, or Decarbazine,
anti-metabolite agents, selected from Pentostatine, Methotrexate, Pemeterxed, Floxuridine, Fluorouracil, Cytaraine, Mercaptopurine or Thiguanine,
cytotoxic antibiotics selected from Rubitecan, Mitomycine C, Daunorubicin, Doxorubicine, Bleomycin, Plicamycin, Mitoxantrone HCl, or Oxaliplatine, or
plant derivatives, selected from Vinorelbine, BMS 184476, Vincristine sulfate, Vinblastine, Docetaxel taxol,
for a simultaneous, separated or sequential administration.

The present invention provides a method to inhibit an enzyme chosen from nitric oxide synthase, in particular endothelial nitric oxide synthase, neuronal nitric oxide synthase, inducible nitric oxide synthase, reductases, in particular P450 reductases, catalases and NADHP oxydases comprising the step of:
mixing a compound of formula (I), wherein the bond A between two aryls of the aforementioned compounds is represented by triple bond, with a biological sample containing said enzyme.

The present invention provides still a method to inhibit an enzyme chosen from nitric oxide synthase, in particular endothelial nitric oxide synthase, neuronal nitric oxide synthase, inducible nitric oxide synthase, reductases, in particular P450 reductases, catalases and NADHP oxydases comprising the step of:

(a) Mixing a compound of formula (I), wherein the bond A between two aryls of the aforementioned compounds is represented by

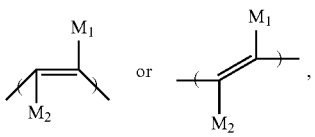

in cis form or cis-trans mixture with a biological sample containing said enzyme, (b) Light irradiating the sample under appropriate conditions to transform the cis form into active compound said trans form.

The present invention is illustrated by the following figures and examples.

FIGURES

FIG. 1A illustrates the synthetic route of example 1 to obtain compound 9 and compound 10, said mixture designed herein after YL3. N-Ethyl aniline is reacted with compound 1 in the presence of NaBH(OAc)$_3$ to obtain compound 2. Compound 2 is transformed to compound 3 in a Vilsmeier's formylation. The Knoevnagel's condensation between 4-nitrophenyl-acetic acid and compound 3 leads to the stilbene derivative compound 4. Compound 5 is obtained from compound 4 by treatment in the presence of NaBH$_4$—HOAc. Compound 6 is an adenosine derivative obtained by oxidation of commercially available 2',3'-isopropylideneadenosine. The coupling between compound 5 and compound 6 to obtain compound 7 is carried out in anhydrous DMF in the presence of HBTU. After deprotection of the isopropylidene motif of compound 7, phosphorylation reaction is carried out in the presence of chlorodiethylphosphate and is followed by an acid hydrolysis reaction to obtain isomeric compounds 9 and 10 herein mentioned as YL3. The two isomers are obtained in a proportion of about 40:60.

Figure 1B:
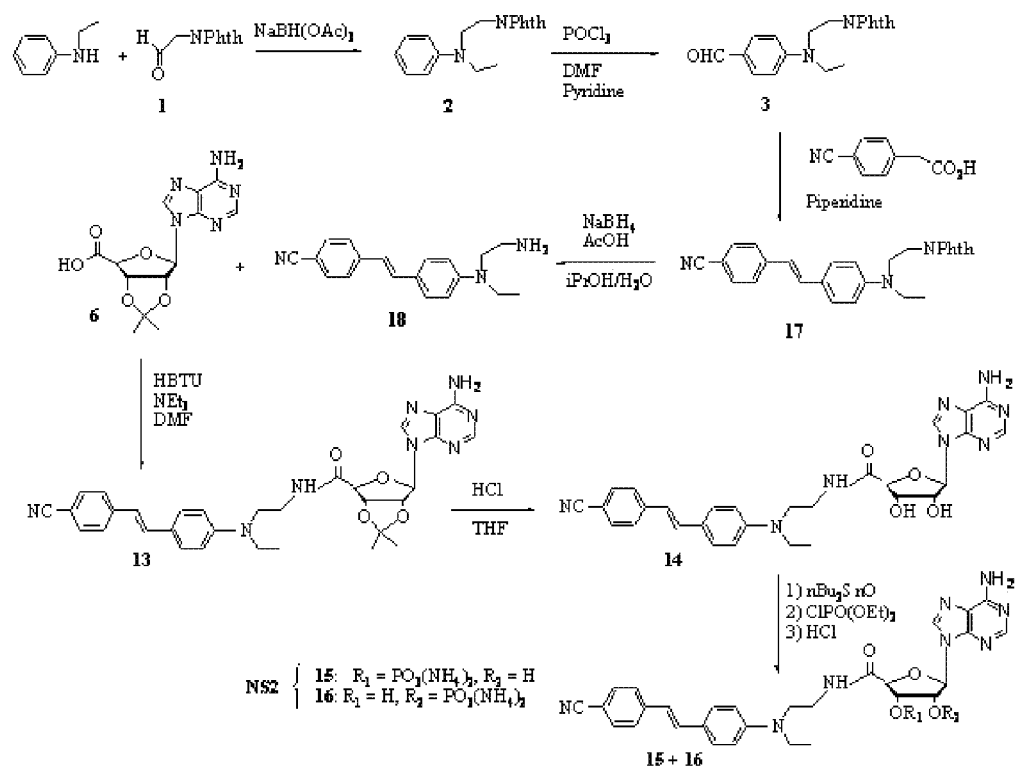

FIG. 1B illustrates the synthetic route to obtain compound 15 and compound 16, said mixture designed herein after NS2. N-Ethyl aniline was reacted with compound 1 in the presence of NaBH(OAc)$_3$ to obtain compound 2. Compound 2 was formylated to compound 3 following a Vilsmeier's reaction. The Knoevnagel's condensation between 4-cyanophenyl-acetic acid and compound 3 led to the stilbene derivative 17. Compound 18 was obtained from compound 17 by treatment in the presence of NaBH$_4$—HOAc. Compound 6 was an adenosine derivative obtained by oxidation of commercially available 2',3'-isopropylideneadenosine. The coupling between compound 18 and compound 6 to obtain compound 13 was carried out in anhydrous DMF in the presence of HBTU. After deprotection of the isopropylidene motif of compound 13, phosphorylation reaction was carried out in the presence of chlorodiethylphosphate and was followed by an acid hydrolysis reaction to obtain a mixture of isomeric compounds 15, 15', 16 and 16' herein mentioned as NS2. The four isomers corresponded to a mixture of Z and E isomeric stilbenes 15 and 16, with the phosphate group on position 2' or 3', in a 30:25:25:20 ratio.

Figure 2A:
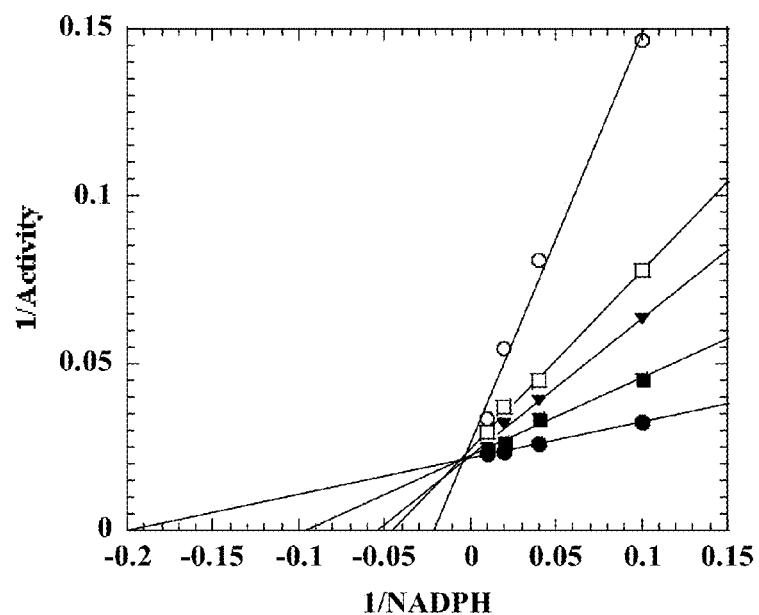

FIG. 2A illustrates the competition between YL3 and NADPH in the inhibition of the formation of NO synthesized by neuronal NO-synthase, according to example 2.1. The formation of NO was measured in the presence of various concentrations of NADPH (10, 25, 50 and 100 µM) and in the absence (●), or in the presence of 5 (■), 25 (▼), 50 (□) or 100 (○) µM YL3.

Figure 2B:
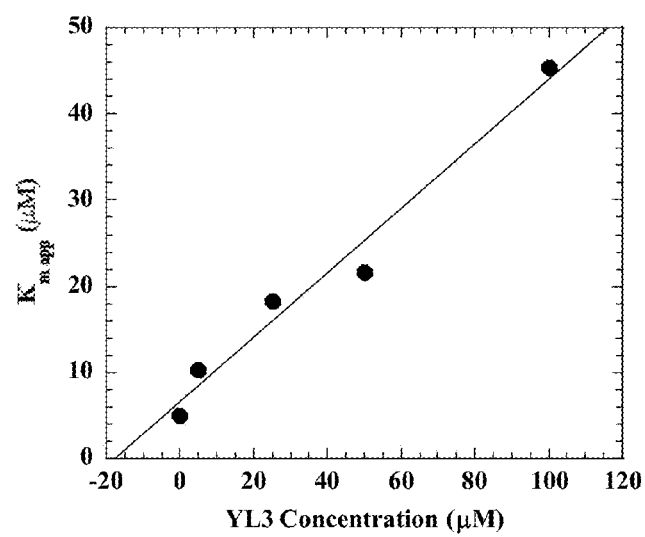

FIG. 2B shows the linear dependence between $K_{m\ app}$ (coordinate axis) and the concentration of YL3 (horizontal axis). Intercept with the x-axis indicates a $K_i$ value of 17 µM. These data are representative of a typical experiment. These data show that the inhibition of the formation of NO catalysed by neuronal NOS is competitive versus cofactor NADPH.

Figure 3A:
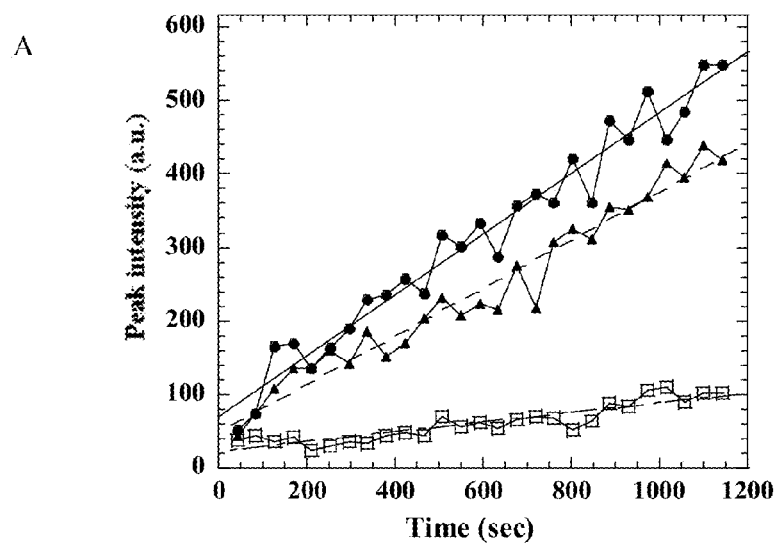

FIG. 3A illustrates the effects of YL3 on the rates of formation of the BocMPO-OOH spin-adduct, according to example 2.4. Productions of $O_2.^-$ by nNOS (in the absence of L-arginine and H$_4$B) were measured by spin-trapping in the presence of BocMPO followed by EPR spectroscopy. The intensities of the second line of the BocMPO-OOH spin-adduct (arrows in FIG. 3B) were reported as a function of time from incubations performed in buffer alone (●, without YL3), or in the presence of 15 µM (▲) or 100 µM YL3 (□). Linear fitting of the data points are shown as (—), (—-) and (- -) respectively. Horizontal axis represents magnetic field intensity. Coordinate axis represents EPR signal intensity. These results show that YL3 inhibits the formation of superoxide anions by nNOS under uncoupling conditions.

Figure 3B:
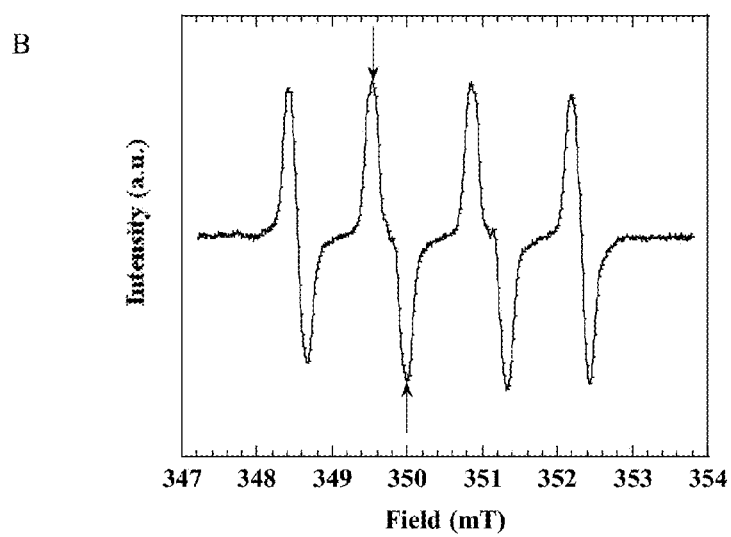

FIG. 3B shows the EPR spectrum of a Boc-MPOOH spin adduct.

Figure 4:
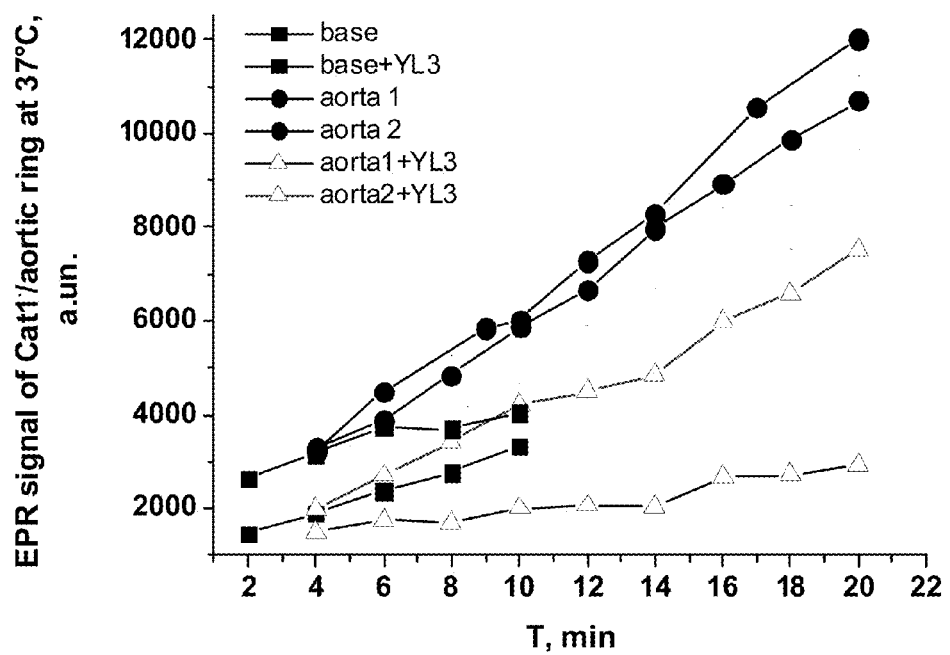

FIG. 4 displays the measurements of superoxide anion production from isolated aortic rings after addition of YL3 (10 µM) or vehicle by the EPR spin probe (Cat1-H), according to example 3. Measurements were performed at 37° C. directly in capillary in the resonator of CW X-band EPR Spectrometer Magnettech MiniScope MS200 equipped with temperature controller. Aortic rings (about 2-mm-long) were obtained from isolated aorta of C57BL/6 mice, male, 15 weeks old. The level of superoxide ions produced extracellularly by isolated aortic rings and detected by the formation of the Cat1. radicals, was monitored in the presence (Δ) or absence (○) of YL3; the basal level corresponds to the vehicle alone in the absence of aortic rings with or without YL3.

Figure 5A:
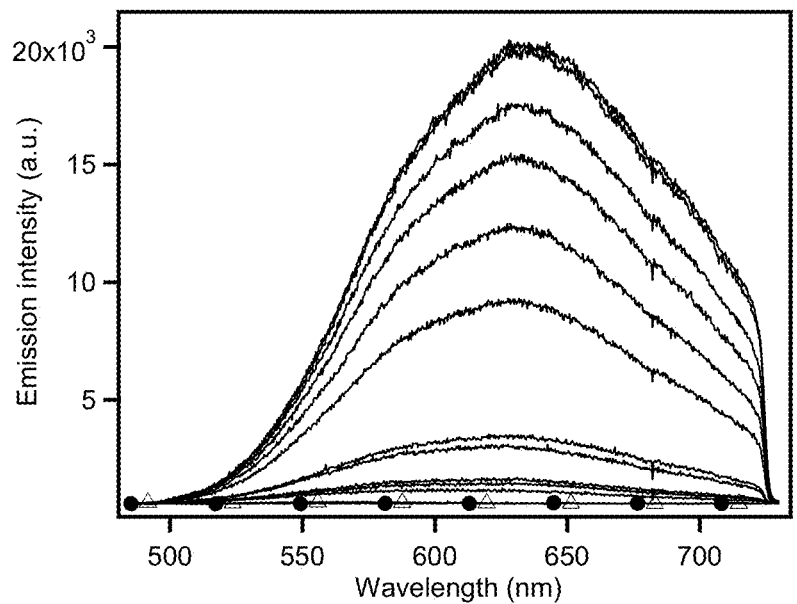

FIG. 5A represents the spectrum of neuronal NOS alone (5 µM) (line with open triangle), or of YL3 alone (30 µM) (line with black circle), or of NOS binding YL3 (using varying concentrations of YL3, from 0 to 30 µM, in the presence of 5 µM NOS) (lines without marker) under two-photons excitation condition ($\lambda_{ex,\ 2\text{-}photons}$=940 nm; the measurements were performed according to the method described in example 4 (part 4.1). Horizontal axis represents fluorescence emission wavelength of samples. Coordinate axis represents fluorescence emission intensity.

Figure 5B:
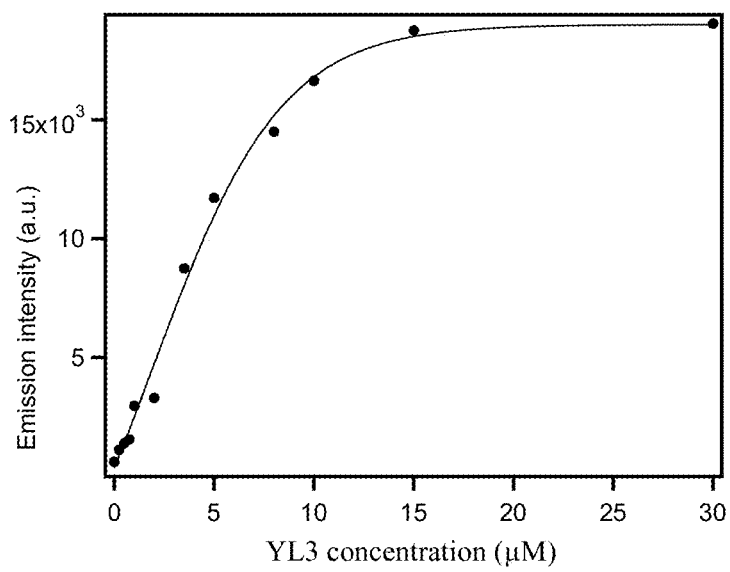

FIG. 5B displays the titration study of YL3-nNOS complex, as typically shown in FIG. 5A. Horizontal axis represents the concentration of YL3 in a sample containing nNOS. Coordinate axis represents YL3-nNOS complex fluorescence emission at 630 nm under two-photons excitation condition a ($\lambda_{ex,\ 2\text{-}photons}$=940 nm).

Figure 6A:
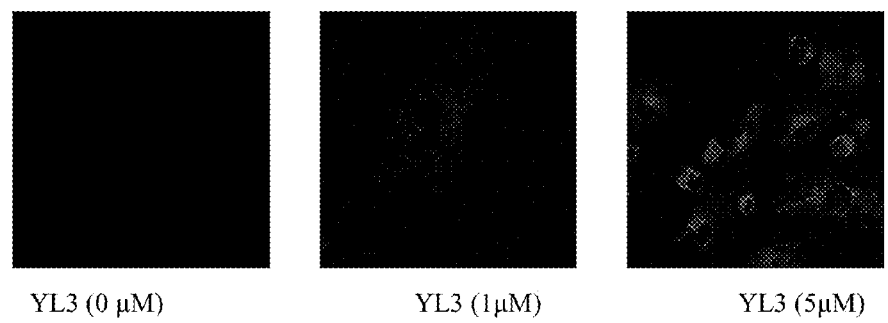

FIG. 6A displays the fluorescence emitted by HUVEC cells observed by two-photons microscopy, according to example 5. The cells are incubated with 1 or 5 µM YL3. The cells culture without YL3 is used as control. The excitation wavelength was 840 nm (Emission: 500-650 nm).

Figure 6B:
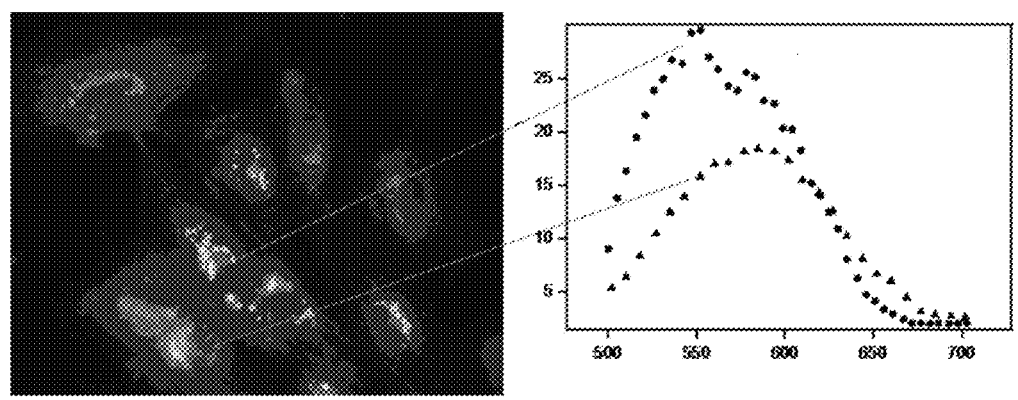

FIG. 6B: The photo at left illustrates epifluorescence imaging obtained in HUVEC cells incubated with YL3. The diagram at right displays fluorescence emission spectra from bright zones (●) or from cytoplasm (▲). Horizontal axis represents the wave length (nm) of fluorescence. Coordinate axis represents fluorescence intensity.

Figure 7:
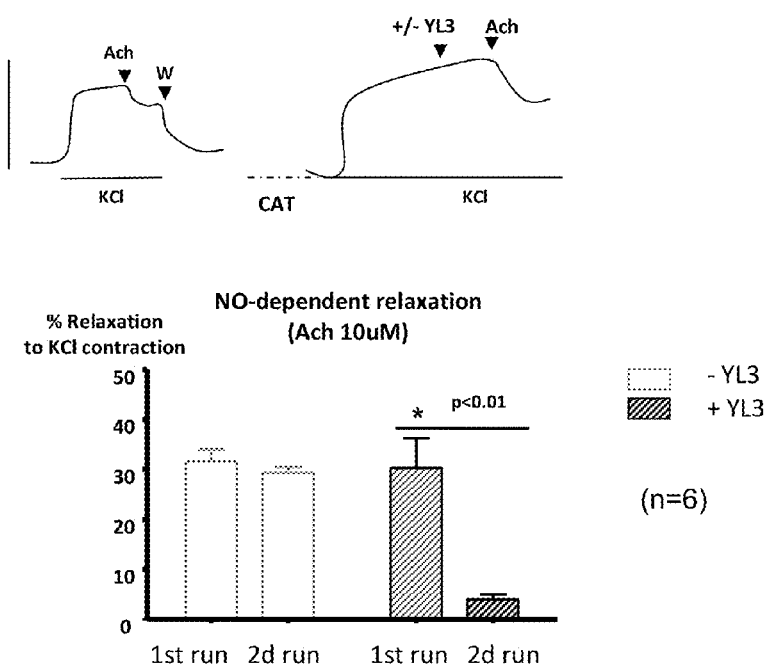

FIG. 7 represents the effect of YL3 (10 µM) on the endothelium-dependant relaxation of mice aorta pre-contracted by KCl. In the presence of catalase, indomethacine (a cycloxygenase inhibitor) and a high potassium extra cell concentration, the relaxation of mice aortic rings, induced by muscarinic receptors stimulation uniquely rest on NO produced by endothelial cells. In this situation, YL3 inhibits the relaxation induced by acetylcholine, as what is expected for an eNOS inhibitor.

Figure 8:
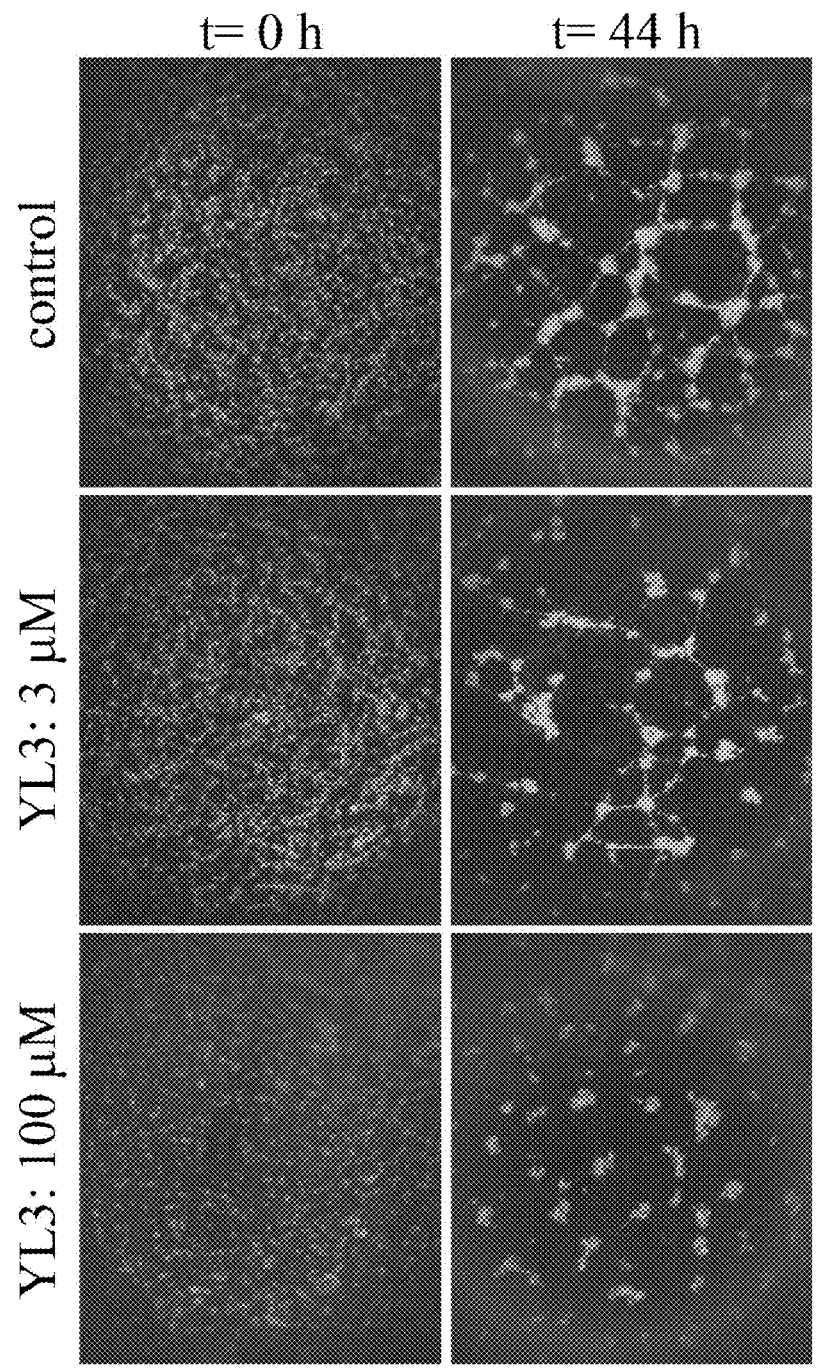

FIG. 8: shows the effect of YL3 (0, 3 or 100 μM) inhibiting the formation of endothelial tube promoted by VEGF treatment, according to example 8. The extent of the endothelial network in the different conditions tested was always compared within a same set of experiments and relative values were used for inter-assays comparisons. Human Umbilical Vein Endothelial Cells (HUVECs) passage 3-5 plated on Matrigel were used in these experiments. The photos of left column show cells before the treatment by different concentration of YL3. The photos of right column show cells after 48 hours treatment by 3 μM or 100 μM YL3, and control sample with VEGF treatment alone.

Figure 9:
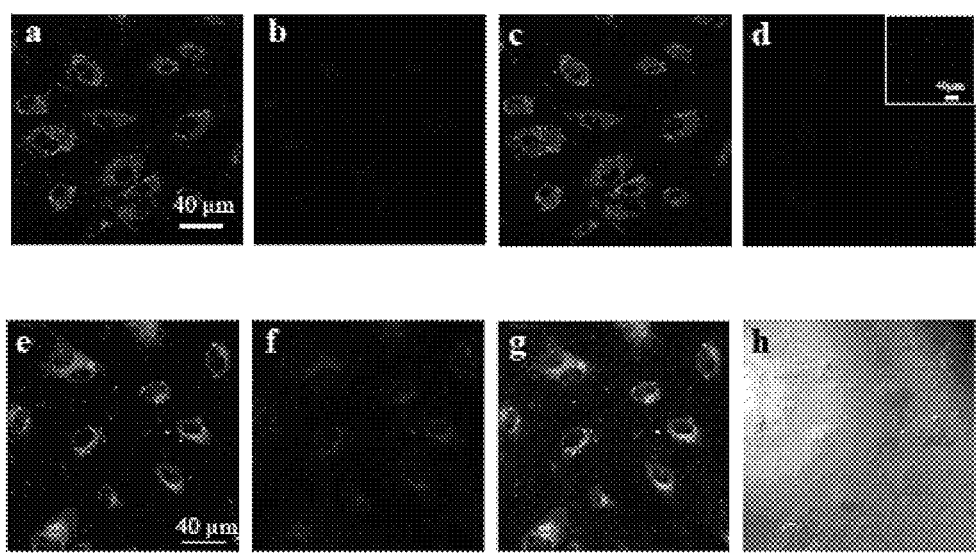

FIG. 9: shows the imaging of living HUVECs using the two-photon fluorescence properties of NS1 and co-localization with the Golgi complex. HUVECs were treated with 5 μM NS1 and further observed under two-photon excitation (840 nm; emission setting: 520-680 nm) (a). Panel b shows the nucleus staining by Hoechst 33342 of NS1-treated HUVECs (two-photon excitation, 740 nm; emission at 410-510 nm). Panel c, merged image of a and b. Panel d, control two-photon image of non-treated HUVECs at the same setting (inset: nucleus staining of control cells). (e-h) Co-localization imaging of NS1 and the Golgi complex: living HUVECs were treated with NS1 (5 μM) and Golgi tracker (BODIPY TR Ceramide; 5 μM) for 60 min. Panel e shows the imaging channel of NS1 (one-photon excitation, 488 nm; emission setting: 520-680 nm). Panel f shows the imaging channel of the Golgi tracker (one-photon excitation, 543 nm; emission setting: 600-650 nm). Panel g, merged image of e and f (with nucleus staining) Yellow areas indicate co-localization of NS1 and the Golgi apparatus. Panel h, corresponding DIC transmission image.

Figure 10:
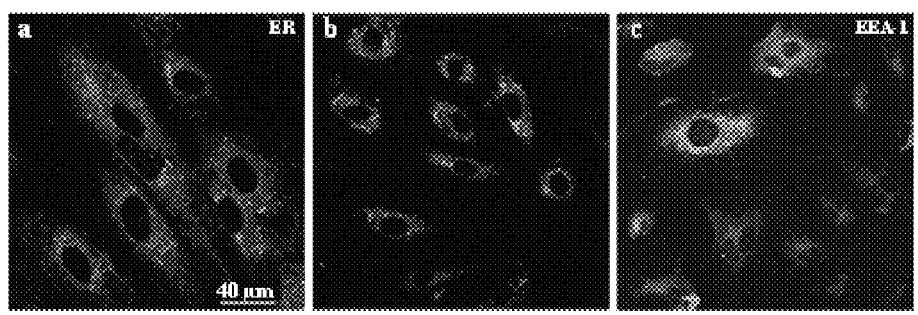

FIG. 10: shows Co-localization imaging of NS1 and Endoplasmic Reticulum (ER), Mitochondria or Early Endosome (EEA1). (a) Merged image of NS1 and ER. (b) Merged image of NS1 and mitochondria. Living HUVECs were treated with NS1 (5 μM) and ER tracker (ER-Tracker™ Red dye; 100 nM) or MitoTracker (MitoTracker® Deep Red FM; 50 nM) for 30 min and further observed under confocal microscopy. (c) Merged image of NS1 and EEA1. Living HUVECs were treated with NS1 (10 μM) for 60 min prior to fixation and immuno-staining of EEA1, and further observed under confocal microcopy. Primary and secondary antibodies for immuno-staining were rabbit polyclonal to EEA1-Early Endosome Marker and Alexa Fluor® 594 donkey anti-rabbit IgG (H+L), respectively. Excitation and emission settings: NS1 (exc. 488 nm; em. 520-680 nm), ER (exc. 543 nm; em. 590-670 nm), mitochondria (exc. 633 nm; em. 650-700 nm), EEA1 (exc. 543 nm; em. 590-700 nm).

Figure 11:
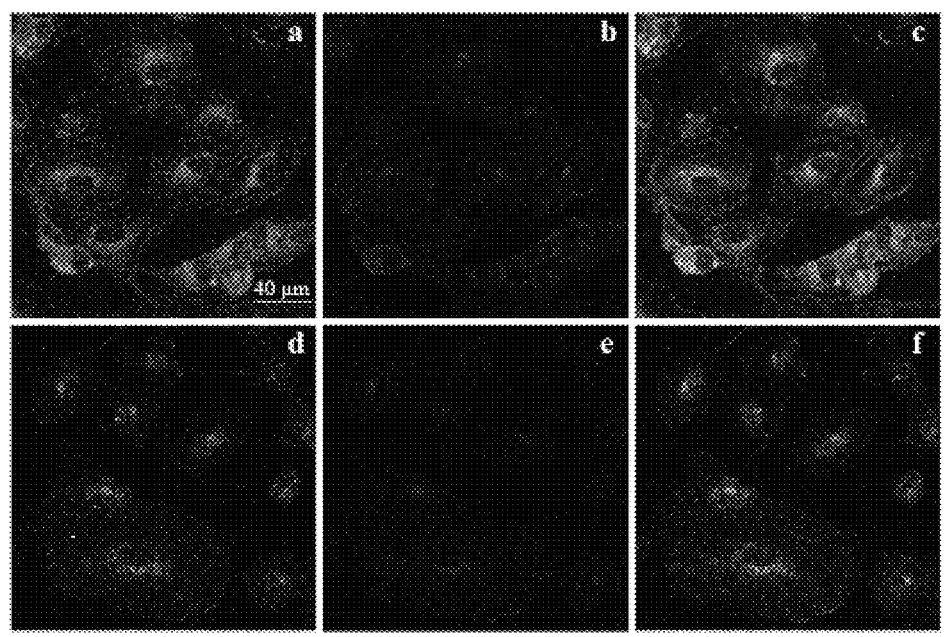

FIG. 11: displays co-localization experiments of NS1 with eNOS. (a-f) Co-localization imaging of NS1 and eNOS. Living HUVECs were treated with NS1 (10 μM) for 60 min prior to fixation and immuno-staining of eNOS. Primary and secondary antibodies for immuno-staining were purified mouse anti-eNOS/NOS Type III and AlexaFluor® 594 goat anti-mouse IgG (H+L), respectively. Panels a and d show the imaging channel of NS1 (one-photon excitation, 488 nm, and two-photon excitation, 840 nm, respectively; emission setting: 520-680 nm). Panel b and e show the imaging channel of eNOS (one-photon excitation, 543 nm; emission setting: 590-700 nm), corresponding to a and d, respectively. Panel c: merged image of a and b. Panel f: merged image of d and e. Yellow to orange areas indicate co-localization of NS1 and eNOS. Nucleus staining by Hoechst 3342 is also shown in panels c and f.

EXAMPLE 1

Molecular Modeling and Synthesis of Mixture YL3

1.1 Molecular Modeling

MD simulation of nNOS-YL3 complex was carried out using the program NAMD (Phillips et al., *J Comput Chem* 2005, 26, 1781-802) with the CHARMM27 force field. The molecular system formed by nNOS rat dimeric enzyme, FAD, FMN (PDB ID 1TLL) and YL3 was centered in a cubic cell of pre-equilibrated TIP3P water model (Jorgensen et al., *J. Chem. Physiol.* 1983, 79, 926-35) molecules. The electrostatic interactions were calculated with no truncation, using the particle mesh Ewald summation algorithm. The system was made electrostatically neutral by randomly adding 20 sodium cations. The van der Waals interactions were smoothly shifted to zero between 10.0 Å and 12.0 Å. The ionic concentration of the system was set to 0.15 M by adding randomly sodium and chloride ions. The list of the non-bonded interactions was truncated at 13.5 Å. The energy of the system was minimized during 5000 steps using the conjugate gradient energy minimization algorithm while the solute atoms were harmonically restraint to their initial positions with a force constant of 50.0 kcal/mol/Å$^2$. The system was further heated linearly to 300 K over 60 ps. The lengths of the bonds containing hydrogen atoms were fixed with the SHAKE algorithm (Ryckaert et al., *J. Comp. Phys.* 1977, 23, 327-41) and the equations of motion were iterated using a time step of 2 fs in the velocity Verlet integrator. Molecular dynamics simulation in standard conditions (NPT) was further used to equilibrate the system and for production run. During the equilibration phase, the restrains applied on the solute atoms were gradually reduced from 5.0 kcal/mol/Å$^2$ to zero. The pressure and temperature were restrained to 1 atm and 300 K, respectively. Two trajectories of 10 ns each were produced for the YL3 complexed to nNOS.

1.2 Synthesis of Compounds 9 and 10 (Herein Called YL3) (FIG. 1A) and of Compounds 15 and 16 (Herein Called N52)(FIG. 1B)

TLC was performed on precoated plates of Silica Gel 60E-254 (Merck); components were detected by UV light. $^1$H and $^{13}$C NMR spectra were recorded with a Bruker Biospin Avance II 250 MHz spectrometer, and chemical shifts refer to an internal standard of Me$_4$Si (δ=0.00). Mass spectra were recorded by electrospray ionization (ESI) in both positive (ESI+) and negative (ESI−) ionization detection modes. Elemental analyses were performed at ICSN (Gif sur Yvette, France) and high-resolution mass spectra (HRMS) were obtained by ESI in time-of-flight (TOF) detection mode on a LCT (Waters-Micromass) spectrometer at ICSN (Gif sur Yvette, France). Phthalimidoacetaldehyde (compound 1) was prepared according to a known procedure (Safavy et al., *Bioconjugate Chem* 2002, 13, 317-26). The carboxylic acid 6 was prepared from 2',3'-isopropylidene adenosine as reported previously (Ha and Nair, Tetrahedron Lett 1996, 37, 1567-70).

Compound 1: HCl (0.1 N, 42 mL) was added to a solution of phthalimidoacetaldehyde diethyl acetal (4.18 g, 15.1 mmol) in AcOH (42 mL). The resulting suspension was heated at 60° C. for 24 h. The solvent was evaporated and the mixture was dissolved in CH$_2$Cl$_2$. The organic phase was washed with sat. aq NaHCO$_3$, H$_2$O, dried over MgSO$_4$ and evaporated to afford the title compound as a brown solid (2.72 g, 95%). The physical data are consistent with the previously reported ones.

Compound 2: NaBH(OAc)$_3$ (3.05 g; 14.4 mmol) was added to a solution of N-ethylaniline (1.16 g; 9.6 mmol) and 2-phthalimidoacetaldehyde (1) (2.72 g, 14.4 mmol) in CH$_2$Cl$_2$ (28 mL). After 24 h at 20° C., CH$_2$Cl$_2$ was added and the organic phase was washed with H$_2$O, dried (MgSO$_4$) and evaporated. The crude product was purified by chromatography over silica gel (80:20 CH$_2$Cl$_2$-cyclohexane) to afford 2 as a yellow solid (2.71 g, 96%). $^1$H NMR (250 MHz, CDCl$_3$): δ 7.85 (m, 2H), 7.71 (m, 2H), 7.24 (t, J=7.8 Hz, 2H), 6.86 (d, J=7.8 Hz, 2H), 6.67 (t, J=7.8 Hz, 1H), 3.91 (dd, J=6.5, 8.1 Hz, 2H), 3.58 (dd, J=6.5, 8.1 Hz, 2H), 3.46 (q, J=6.9 Hz, 2H), 1.22 (t, J=7.0 Hz, 3H). $^{13}$C NMR (63 MHz, CDCl$_3$): δ 168.0 (C), 147.2 (C), 133.7 (CH), 131.8 (C), 129.2 (CH), 123.0 (CH), 116.0 (CH), 111.9 (CH), 47.8 (CH$_2$), 44.6 (CH$_2$), 35.0 (CH$_2$), 12.2 (CH$_3$). MS: m/z=295 (MH$^+$). Anal. calcd for C$_{18}$H$_{18}$N$_2$O$_2$ (294.14), C, 73.45, H, 6.16, N, 9.52. Found C, 73.33, H, 6.17, N, 9.62.

Compound 3: Phosphorus oxychloride (POCl$_3$, 5.24 mL) was added dropwise to a solution of compound 2 (2.71 g, 9.2 mmol) in anhydrous pyridine (4.50 mL) and DMF (55 mL), at 0° C. under an Ar atmosphere. After 24 h at RT, ice (~600 g) was added and stirred for 30 min. The precipitate was filtered, washed and dissolved with CH$_2$Cl$_2$. The organic phase was separated from H$_2$O, dried (MgSO$_4$) and evaporated. The crude product was filtered over silica gel (Et$_2$O) to afford 3 as a pale yellow solid after evaporation of the solvent (2.84 g, 96%). $^1$H NMR (250 MHz, CDCl$_3$): δ 9.67 (s, 1H), 7.82 (m, 2H), 7.69 (m, 4H), 6.81 (d, J=8.9 Hz, 2H), 3.89 (dd, J=6.6, 7.3 Hz, 2H), 3.63 (dd, J=6.6, 7.3 Hz, 2H), 3.50 (q, J=7.3 Hz, 2H), 1.21 (t, J=7.3 Hz, 3H). $^{13}$C NMR (63 MHz, CDCl$_3$): δ 189.9 (CH), 168.0 (C), 152.0 (C), 134.0 (C), 132.1 (CH), 131.6 (C), 125.2 (C), 123.2 (CH), 111.8 (CH), 47.6 (CH$_2$), 44.9 (CH$_2$), 34.6 (CH$_2$), 12.1 (CH$_3$). MS: m/z=323 (MH$^+$). Anal. calcd for C$_{19}$H$_{18}$N$_2$O$_3$ (322.13), C, 70.79, H, 5.63, N, 8.69. Found C, 70.28, H, 5.62, N, 8.62.

Compound 4: A solution of 4-nitrophenyl acetic acid (1.55 g, 8.6 mmol) and piperidine (655 mg, 7.7 mmol) in CH$_2$Cl$_2$ (~10 mL) was stirred at RT for 10 min, and compound 3 (2.48 g, 7.7 mmol) was added to the mixture. After 10 min at RT, CH$_2$Cl$_2$ was evaporated and the reaction was heated at 100° C. under vacuum (15 mmHg) for 3 h, then at 150° C./15 mmHg for 3 h. The crude product was purified by chromatography over silica gel (80:20 CH$_2$Cl$_2$-cyclohexane) to afford 4 as a red solid (2.21 g, 65%). $^1$H NMR (500 MHz, CDCl$_3$): δ 8.16 (d, J=8.9 Hz, 2H), 7.83 (m, 2H), 7.70 (m, 2H), 7.53 (d, J=8.9 Hz, 2H), 7.40 (d, J=8.8 Hz, 2H), 7.14 (d, J=16.2 Hz, 1H), 6.87 (d, J=16.2 Hz, 1H), 6.80 (d, J=8.9 Hz, 2H), 3.88 (dd, J=6.7, 8.1 Hz, 2H), 3.58 (dd, J=6.7, 8.1 Hz, 2H), 3.46 (q, J=7.0 Hz, 2H), 1.20 (t, J=7.0 Hz, 3H). $^{13}$C NMR (63 MHz, CDCl$_3$): δ 168.3 (C), 148.0 (C), 145.9 (C), 145.0 (C), 134.1 (CH), 133.5 (CH), 132.0 (C), 128.7 (CH), 126.1 (CH), 124.5 (C), 124.1 (CH), 123.3 (CH), 121.7 (CH), 112.1 (CH), 48.0 (CH$_2$), 45.1 (CH$_2$), 35.1 (CH$_2$), 12.4 (CH$_3$). MS: m/z=442 (MH$^+$). Anal. calcd for C$_{26}$H$_{23}$N$_3$O$_4$ (441.17), C, 70.73, H, 5.25, N, 9.52. Found C, 70.19, H, 5.13, N, 9.53.

Compound 5: NaBH$_4$ (806 mg, 21.5 mmol) was added to a suspension of 4 (1.88 g, 4.3 mmol) in isopropanol/water (6/1, 120 mL). After 1 h at 60° C., acetic acid (8 mL) was added at RT and the reaction was kept at 80° C. for 48 h. Isopropanol was evaporated and the precipitate was filtered. The crude product was purified by chromatography over silica gel (MeOH:CH$_2$Cl$_2$: NH$_4$OH=3:97:0.25) to afford 5 as a red solid (1.02 g, 77%). $^1$H NMR (250 MHz, DMSO-d$_6$): δ 8.17 (d, J=8.9 Hz, 2H), 7.75 (d, J=8.9 Hz, 2H), 7.49 (d, J=8.9 Hz, 2H), 7.41 (d, J=16.4 Hz, 1H), 7.10 (d, J=16.4 Hz, 1H), 6.76 (d, J=8.9 Hz, 2H), 3.42 (m, 4H), 2.83 (t, J=6.6 Hz, 2H), 1.09 (t, J=7.0 Hz, 3H). $^{13}$C NMR (63 MHz, DMSO-d$_6$): δ 148.1 (C), 145.2 (C), 145.1 (C), 133.9 (CH), 128.7 (CH), 126.3 (CH), 124.0 (CH), 123.6 (C), 120.9 (CH), 111.6 (CH), 49.8 (CH$_2$), 44.4 (CH$_2$), 37.8 (CH$_2$), 12.0 (CH$_3$). HRMS (ESI) calculated for C$_{18}$H$_{22}$N$_3$O$_2$ (MH$^+$) m/z 312,1712. found 312,1701.

Compound 7: Et$_3$N (0.8 mL) and HBTU (2.18 g, 5.7 mmol) were added to a solution of 5 (1.19 g, 3.8 mmol) and uronic acid 6 (1.23 g, 3.8 mmol) in anhydrous DMF (130 mL).

After 48 h at RT under an Ar atmosphere, DMF was evaporated and the usually work-up with EtOAc/H$_2$O gave the crude product which was purified by chromatography over silica gel (60:40 EtOAc-CH$_2$Cl$_2$) to afford 7 as a red solid (1.64 g, 70%). $^1$H NMR (250 MHz, DMSO-d$_6$): δ 8.29 (s, 1H), 8.17 (d, J=8.8 Hz, 2H), 8.11 (s, 1H), 7.75 (d, J=8.8 Hz, 2H), 7.72 (s, 1H, D$_2$O exchangeable), 7.45 (d, J=8.8 Hz, 2H), 7.39 (d, J=16.4 Hz, 1H), 7.33 (s, 2H, D$_2$O exchangeable), 7.08 (d, J=16.4 Hz, 1H), 6.67 (d, J=8.8 Hz, 2H), 6.37 (d, J=1.6 Hz, 1H), 5.43 (dd, 1H, J=1.9, 6.1 Hz, 1H), 5.40 (dd, 1H, J=1.6, 6.1 Hz, 1H), 4.57 (d, J=1.9 Hz, 1H), 3.31-3.24 (m, 6H), 1.54 (s, 3H), 1.34 (s, 3H), 1.03 (t, J=7.0 Hz, 3H). $^{13}$C NMR (63 MHz, DMSO-d$_6$): δ 168.9 (C), 156.0 (C), 152.4 (CH), 148.8 (C), 148.1 (C), 145.3 (C), 145.1 (C), 140.5 (CH), 133.9 (CH), 128.7 (CH), 126.2 (CH), 124.0 (CH), 123.4 (C), 120.7 (CH), 118.9 (C), 112.9 (C), 111.3 (CH), 89.5 (CH), 86.0 (CH), 83.2 (CH), 83.1 (CH), 47.7 (CH$_2$), 44.2 (CH$_2$), 35.7 (CH$_2$), 26.7 (CH$_3$), 25.0 (CH$_3$), 12.0 (CH$_3$). MS: m/z=615 (MH$^+$). Anal. calcd for C$_{31}$H$_{34}$N$_8$O$_6$ (614.26), C, 60.58; H, 5.58; N, 18.23. Found C, 59.98; H, 5.53; N, 18.11.

Compound 8: HCl (1M, 20 mL) was added to a solution of 7 (0.75 g, 1.2 mmol) in THF (30 mL). After 24 h at 60° C., sat. K$_2$CO$_3$ was added up to pH~10 and THF was evaporated off. The precipitate was filtered, washed (pH~7) and dried to afford 8 as a red solid (0.67 g, 96%). $^1$H NMR (250 MHz, DMSO-d$_6$): δ 9.16 (bt, 1H, D$_2$O exchangeable), 8.37 (s, 1H), 8.18 (d, J=8.9 Hz, 2H), 8.08 (s, 1H), 7.76 (d, J=8.9 Hz, 2H), 7.48 (d, J=8.5 Hz, 2H), 7.41 (d, J=16.3 Hz, 2H), 7.09 (d, J=16.3 Hz, 2H), 6.78 (d, J=8.5 Hz, 2H), 5.97 (d, J=7.3 Hz, 1H), 5.78 (d, J=4.3 Hz, 1H, D$_2$O exchangeable), 5.57 (d, J=6.2 Hz, 1H, D$_2$O exchangeable), 4.62 (m, 1H), 4.33 (bs, 1H), 4.17 (dd, J=4.3, 3.5 Hz, 1H), 3.42 (m, 6H), 1.08 (t, J=6.9 Hz, 3H). $^{13}$C NMR (125 MHz, DMSO-d$_6$): δ 170.0 (C), 161.8 (C), 156.2 (C), 152.6 (CH), 149.0 (C), 148.2 (C), 145.4 (C), 145.3 (C), 140.8 (CH), 134.1 (CH), 128.9 (CH), 126.4 (CH), 124.2 (C), 123.6 (CH), 120.9 (CH), 111.6 (CH), 87.9 (CH), 84.7 (CH), 73.0 (CH), 71.9 (CH), 48.7 (CH$_2$), 44.6 (CH$_2$), 36.5 (CH$_2$), 12.1 (CH$_3$). HRMS (ESI) calculated for C$_{28}$H$_{31}$N$_8$O$_6$ (MH$^+$) m/z 575,2367. found 575,2386.

Mixture YL3 (Compounds 9+10): nBu$_2$SnO (52 mg, 0.21 mmol) was added to a suspension of 8 (93 mg, 0.16 mmol) in anhydrous toluene (10 mL). After 2 h at 130° C. under an Ar atmosphere, toluene was evaporated Anhydrous CH$_2$Cl$_2$ (10 mL) and ClP(O)(OEt)$_2$ (47 μL, 0.32 mmol) were added to the reaction. After 48 h at RT, CH$_2$Cl$_2$ was evaporated off. THF (3 mL) and HCl (37%, 1.5 mL) were added and the mixture was stirred at RT for 2.5 h (TLC monitoring: 30:65:4:1 CH$_3$OH—CH$_2$Cl$_2$-H$_2$O-Et$_3$N). After addition of an aq. NH$_3$ solution (2%, until pH~7), the deep-red solid was filtered, washed with H$_2$O. The crude product was dissolved in DMF and purified by chromatography over C$_{18}$ silica gel (25:75:1 CH$_3$CN—H$_2$O-2% NH$_4$OH) to provide a mixture of the two isomeric compounds 9 and 10 in a ratio of 40:60 after lyophilization (76 mg, 70%).

2-PO$_4$H$_2$ (compound 9): $^1$H NMR (500 MHz, DMSO-d$_6$): δ 9.16 (bt, 1H), 8.40 (s, 1H), 8.17 (d, 2H, J=8.9 Hz), 8.02 (s, 1H), 7.76 (d, 2H, J=8.9 Hz), 7.48 (d, 2H, J=9.1 Hz), 7.40 (m, 3H), 7.10 (d, 2H, J=16.4 Hz), 6.78 (d, 2H, J=9.1 Hz), 6.07 (d, 1H, J=7.1 Hz), 4.83 (m, 1H), 4.49 (d, 1H, J=3.8 Hz), 4.45 (bs, 1H), 3.44-3.35 (m, 6H), 1.09 (t, 3H, J=7.0 Hz).

3-$PO_4H_2$ (compound 10): $^1$H NMR (500 MHz, DMSO-$d_6$): δ 9.26 (bt, 1H), 8.40 (s, 1H), 8.17 (d, 2H, J=8.9 Hz), 8.02 (s, 1H), 7.76 (d, 2H, J=8.9 Hz), 7.48 (d, 2H, J=9.1 Hz), 7.40 (m, 3H), 7.10 (d, 2H, J=16.4 Hz), 6.78 (d, 2H, J=9.1 Hz), 5.97 (d, 1H, J=8.2 Hz), 4.62 (m, 1H), 4.71 (m, 1H), 4.36 (bs, 1H), 3.44-3.35 (m, 6H), 1.09 (t, 3H, J=7.0 Hz).

$^{13}$C NMR (125 MHz, DMSO-$d_6$): δ169.9 (C), 169.5 (C), 156.2 (C), 152.4 (CH), 148.9 (C), 148.0 (C), 145.3 (C), 145.0 (C), 140.5 (CH), 134.0 (CH), 128.8 (CH), 126.2 (CH), 124.0 (CH), 123.4 (C), 120.8 (CH), 111.4 (CH), 88.3 (CH), 83.9+ 83.6 (CH), 75.7 (CH), 72.3 (CH), 48.7+48.6 ($CH_2$), 44.8+ 44.5 ($CH_2$), 36.4 ($CH_2$), 12.0 ($CH_3$). HRMS (ESI−) calculated for $C_{28}H_{30}N_8O_9P$ [M-H]$^-$ 653,1873. found 653,1877.

EXAMPLE 2

Enzymatic Assays 2.1 Inhibition by YL3 of NO Formation Catalysed by nNOS

Experience Protocol

The initial rates of NO synthesis were determined at 37° C. in 1-cm pathlength cuvettes using the oxyhemoglobin assay for NO (Murphy et Noack, *Methods Enzymol.* 1994, 233, 240-50). Usual incubation mixtures were performed in a total volume of 150 µL containing 50 mM Hepes buffer (pH 7.4), 0.1 M KCl supplemented with DTT (5 mM), oxyhemoglobin (10-20 µM), 1000 U/mL each of SOD and catalase, $H_4B$ (10 µM), L-arginine (100 µM), $CaCl_2$ (1 mM), CaM (10 µg/mL), NADPH (usually 1 mM), and increasing concentration of YL3 (0-100 µM). The mixtures were preincubated for 2 min at 37° C. prior to initiation of the reaction by the addition of 2-5 µL aliquots of nNOS (50-70 nM) to the sample cuvette. The NO-mediated conversion of oxyhemoglobin to methemoglobin was monitored on a Uvikon 941 spectrophotometer by repetitive scanning between 380 and 480 nm every 0.2 min and quantitated using an extinction coefficient of 77 mM$^{-1}$·cm$^{-1}$ between peak at 401 nm and valley at 420 nm (Murphy et Noack, *Methods Enzymol.* 1994, 233, 240-50). The production of NO was linear over all the entire reaction time. Control incubations were performed in the presence of similar amounts of buffer without inhibitor, or in the presence of 100 µM $N^ω$-$NO_2$-L-arginine (a potent inhibitor of NOS) for background determinations. All values are expressed relative to the control and as the mean±S.D. from 3-4 experiments.

Experience Results

Kinetic study performed in the presence of several concentrations of NADPH (10, 25, 50 and 100 µM) and YL3 (0, 5, 25, 50 and 100 µM) shows that mixture YL3 modifies NADPH apparent $K_m$ value without significant effect on apparent $V_m$ (FIGS. 2A, 2B). In a typical experiment shown on FIG. 2, a $K_i$ value of 17 µM has been obtained for this inhibition.

2.2 Inhibition by YL3 of the Reduction of Cytochrome c Catalyzed by nNOS

Experience Protocol

The effects of YL3 on the initial rates of cytochrome c reduction catalyzed by nNOS were spectrophotometrically quantified by measuring the increase in the absorbance at 550 nm, using an extinction coefficient of 21 mM$^{-1}$·cm$^{-1}$. Standard incubation conditions were performed in 1-cm path length cuvettes (total volume of 150 µL) containing 50 mM Hepes buffer (pH 7.4), 0.1 M KCl, L-arginine (100 µM), $CaCl_2$ (1 mM), CaM (10 µg/mL), NADPH (100 µM), and increasing concentration of YL3 (0-100 µM) dissolved in Hepes buffer. The mixtures were preincubated for 2 min at 37° C. before the initiation of the reaction by addition of 2-5 µL aliquots of nNOS.

Experience Results

Experiments performed in the presence of several concentrations of NADPH (10, 25, 50 and 100 µM) and YL3 (0, 5, 25, 50 and 100 µM) show that mixture YL3 modifies NADPH apparent $K_m$ value without significant effect on apparent $V_m$ and $K_i$ values of 25±5 µM have been obtained (data not shown).

2.3 Inhibition by YL3 of Hydrogen Peroxide Formation by nNOS

Experience Protocol $H_2O_2$ released by nNOS was determined by measuring the oxidation of ferrous thiocyanate to ferric thiocyanate as previously described (Heinzel et al., Biochem J 1992, 281, 627-30). The reaction mixture (final volume 100 µL) contained NADPH (200 µM), $CaCl_2$ (1.0 mM), and CaM (10 µg/mL) in 50 mM Hepes buffer pH 7.4. The incubation was initiated by the addition of 2-5 µL aliquots of nNOS (50-70 nM) and stopped after 10 min at 37° C. by the addition of 20 µL of 6M HCl. 10 µL of 0.5 M $NH_4SCN$ (in water) and 50 µL of $Fe(SO_4)_2$ (freshly prepared in deoxygenated water) were added to the mixture. After 10 min at room temperature, the absorbance at 492 nm of the ferric thiocyanate complex formed via $H_2O_2$ oxidation was read on a microplate reader. The $H_2O_2$ release was determined by comparison with a calibration curve using known amounts of $H_2O_2$ (0-25 µM) under the same conditions, except for the absence of nNOS. The concentration of $H_2O_2$ was spectrophotometrically determined using $\epsilon_{240\ nm}$=39.4 M$^{-1}$·cm$^{-1}$.

Experience Results

Experiments show that mixture YL3 inhibits the formation of hydrogen peroxide under the conditions of nNOS uncoupling (data not shown).

2.4 Inhibition by YL3 of Superoxide Formation by nNOS Measured by Spin Trapping and Electron Paramagnetic Resonance Spectroscopy In the absence of substrate L-arginine and cofactor $H_4B$, nNOS generates reactive oxygen species (ROS) such as $H_2O_2$ and superoxide anion that result from dioxygen reduction by flavins and by iron of the heme without formation of NO (uncoupling). The generation of $O_2.^-$ by nNOS under several conditions was monitored by EPR spectroscopy using spin-trapping experiments in the presence of the cyclic nitrone BocMPO.

Experience Protocol

The spin trap 5-tert-butyloxycarbonyl 5-methyl-1-pyrroline N-oxide (BocMPO) was synthesized using a described procedure (Zhao et al., Free Radic Biol Med 2001, 31, 599-606). A typical incubation mixture contained 1 mM NADPH, 1.0 mM $CaCl_2$, CaM (10 µg/mL), and 50 mM BocMPO in 50 mM Hepes buffer pH 7.4. 5-10 µL of nNOS (100-150 nM) were mixed with the previous mixture that was rapidly transferred into an Aqua-X sample cell fitted in a shq001 cavity (Bruker, Wissembourg, France). Data accumulation was started immediately. All measurements were carried out at 21° C. in a Bruker EPR Elexsys 500 spectrometer operating at X-band frequency (9.82 GHz). The following instrument settings were used: field modulation frequency, 100 kHz; field modulation amplitude, 0.2 mT; time constant, 0.081 s; microwave power, 5.1 mW; scan time, 41.9 s; number of scans, 27. BocMPO-OOH and BocMPO-OH spectra were identified by comparison with incubations performed in the presence of xanthine/xanthine oxidase (for BMPO-OOH) as previously described (Zhao et al., Free Radic Biol Med 2001, 31, 599-606). As expected, the BocMPO-OOH spin adduct spontaneously decomposed to the BocMPO-OH spin adduct with a half-life of about 15 min, and its formation was completely abolished in the presence of SOD. The relative amounts of BocMPO-OOH and BocMPO-OH adducts observed in the incubation mixtures were estimated by X-sophe software simulations (Bruker). The second peaks of the BocMPO-OOH and BocMPO-OH adducts are superimposed (maximum, 348.8 mT; minimum, 349.2 mT), and the amplitude of this peak was used to quantify the amounts of superoxide generated in our incubations. The term "BocMPO-OOH spin adduct" will be used instead of "BocMPO-OOH and BocMPO-OH spin adducts" for sake of brevity.

Experience Results

In the absence of L-arginine and $H_4B$, the characteristic 4-line features corresponding to the BocMPO-OOH spin-adduct (a nitroxide) were clearly observed (FIG. 3B) and their intensity increased in a time-dependent manner (FIG. 3A). The rate of formation of the BocMPO-OOH spin-adduct was strongly reduced by the addition of 100 μM L-arginine and 10 μM $H_4B$ (data not shown). As observed on FIG. 3A, the addition of 15 μM YL3 to the reaction mixture significantly reduced the rate of formation of the EPR signal of the BocMPO-OOH spin-adduct and the addition of 100 μM YL3 fully abolished its EPR signal without formation of other paramagnetic species.

EXAMPLE 3

Effects of YL3 on Superoxide Anion Production from Isolated Aortic Rings Measured by EPR Spin Trapping Experience Protocol Formation of $O_2^-$. from isolated aortic rings was assayed by EPR spin trapping using 1-Hydroxy-2,2,6,6-tetramethylpiperidin-4-yl-trimethylammonium chloride (CAT1-H, Alexis Biochemical Inc.). Thoracic aortas were dissected from anesthetized C57BL/6 mice (male, 15 weeks old), cleaned from connective tissues and fat, and cut into small rings (about 2-mm-long). Aortic rings were preincubated in KREBS-DTPA-Hepes buffer (0.1 mmol/liter DTPA, 10 mmol/liter HEPES, pH 7.5), and, after addition of CAT1-H (5 mM) and YL-3 (10 μM) or vehicle, were inserted into capillary (micropipettes, 50 μL, Blaubrand®) which were placed directly in the resonator of CW X-band EPR spectrometer (Magnettech MiniScope MS200), equipped with a temperature controller (37° C.). The formation of the radical (CAT1.) was monitored for 20 minutes and rate of superoxide anion formation was quantified after subtraction of basal signal and normalization to weight of dry tissue.

Experience Results

The ex vivo experiments carried out in mice aortic ring show that mixture YL3 (10 μM) inhibits the synthesis of reactive oxygen species (ROS). The synthesized ROS can be detected after the reaction with hydroxylamine CAT 1-H which is oxidized to nitroxide CAT 1 measured by EPR. The result displayed in FIG. 4 shows that YL3 inhibits NADPH-dependent superoxide production from the NADPH oxydase activity of NO-synthases and of other enzymes which depend on the presence of NADPH in vessels.

EXAMPLE 4

Spectroscopic Methods: Characterization of Y13 Free or Bound to NOS 4.1 Experience Protocols:
Absorption Spectrum UV-visible absorption spectrum was carried out with a Uvikon XL spectrophotometer.

1-Photon Fluorescence in vitro

One-photon fluorescence excitation and emission spectra were recorded on a Eclipse (Varian) spectrofluorimeter, equipped with a thermostated cell holder, using aerated 80 μl solutions placed in micro cells (Hellma, France). The emission spectra were recorded with excitation and emission slits set of 5 nm.

2-Photon Fluorescence In Vitro & Determination of 2-Photon Cross Section

Two-photon excitation and emission spectra were recorded using a home-built set-up consisting of a 80-MHz mode-locked Mai Tai® Ti:Sapphire tunable laser (690-1040 nm, 100 fs laser pulse, Spectra Physics, Mountain View, Calif.) focused on the sample (80 μl placed into a quartz micro cell). The two-photon fluorescence was collected at 90 degrees and was further filtered by a Semrock FF01-842/SP filter—to reject the residual excitation light—. The fluorescence signal was focused into an optical fiber connected to a SpectraPro-275 digital spectrograph (300 lines/mm) coupled to a liquid nitrogen cooled CCD detector (1024×256 pixels; Princeton Instruments, Acton, Mass.). The wavelength calibration of the spectrograph was done using a high pressure mercury lamp. Excitation power was set between 50 and 100 mW and the acquisition time was between 1 and 60 s.

4.2 Experience Results

Spectroscopic and Fluorescence Properties of YL3—YL3 dissolved in DMSO was characterized by an absorption maximum at 460 nm (molar extinction coefficient, 21,000 $M^{-1} \cdot cm^{-1}$). Upon excitation at 460 nm, YL3 was found to be fluorescent in DMSO with an emission peak centered at 740 nm. However, the fluorescence emission was strongly sensitive to solvent polarity and in water or Tris buffer pH 7.5, the fluorescence emission was very weak. The same behaviour was observed under two-photon excitation ($\lambda_{ex}=940$ nm) with a significant two-photon fluorescence emission of YL3 centered at 740 nm, observed only in DMSO while no emission was evidenced in Tris buffer pH 7.5. The two-photon cross-section was found to be equal to 50 GM in DMSO (data not shown).

Fluorescence properties of the YL3-NOS complex—Under one-photon excitation conditions, the emission properties of the YL3-NOS complex was rather difficult to interpret due to the overlapping between the intrinsic fluorescence of NOS and the fluorescence of YL3. As the two-photons fluorescence of NOS protein is intrinsically weak, the two-photon emission was more appropriate for monitoring the fluorescence recovery of YL3 upon binding to NOS. Indeed, as shown in FIG. 5A, the fluorescence of NOS was non detectable upon two-photon excitation. FIG. 5A also confirms that YL3 is not fluorescent in Tris buffer. However, the fluorescence emission of YL3 continuously increased in the presence of nNOS. As the contribution of nNOS to the overall spectrum is negligible, the emission intensity actually accounts for the YL3-NOS complex formation.

EXAMPLE 5

2-Photon Imaging and Epifluorescence Imaging of HUVEC Cells 5.1 Two Photons Microscopy Protocol Two-photon microscopy was performed using the Leica TCS-SP2 confocal microscope equipped with a 10 watt Spectra-Physics Mai-Tai femtosecond pulsed infra-red laser (720-920 nm) as the excitation source. The excitation wavelength was 840 nm (Emission: 500-650 nm).

Epifluorescence imaging was performed using the Hg lamp of the Leica TCS-SP2 confocal microscope (Excitation: 450-490 nm—Emission: 500-650 nm).

5.2 Two-photons Microscopy Results

The penetration of YL3 in HUVEC cells can be observed very quickly, just a few minutes after incubation of cells with YL3 compound and the optimal intracellular signal was obtained with 5 μM YL3 (FIG. 6A). Cytoplasmic fluorescence signal is heterogeneous. The heterogeneity of fluorescent signal can be confirmed by distinct emission spectra which are obtained according to observed zones (FIG. 6B).

EXAMPLE 6

Cell Viability and Vascular Studies 6.1 Protocol of Cell Viability Assay Using the MTT Reagent HUVEC (endothelial) and A7r5 (smooth vascular) cells ($3\times10^4$ cells/well) were cultured in 12-well plates at 37° C. for 1 day in MEM. Serial dilutions of YL3 (1 μM-1 mM) were added to the cells that were further incubated at 37° C. for 24 or 48 hours. MTT analysis was performed based on the standard method, as described previously [see below]. At the end of the kinetics, 20 μl of MTT reagent (3-[4,5-dimethylthiazol-2-yl]-2,5-diphenyl tetrazolium bromide, 7.5 mg/ml, Sigma) was added to the cells and further incubated at 37° C. for 1 h. After cell washing, 100 μl of DMSO was added in each well. The absorbance was measured at 560 nm with subtraction of the blank value at 670 nm using a Wallac Plate Reader (PerkinElmer). In addition, tests using the crystal violet reagent detecting living cells were also performed and cell growth (thermostated at 37° C.) was recorded by videomicroscopy (Axiocam). Cell viability was determined using the 3-(4,5-dimethylthiazoil-2-yl)-2,5-diphenyl tentrazolium bromide (MTT) reduction assay. MTT is reduced in metabolically active cells to yield an insoluble purple formazan product. Cells were cultured in 96-well culture dishes with various concentrations of YL3 (1, 3, 10, 30, or 100 μmol/L). After 2-h incubation, 100 μL per well of a MTT solution (5 mg/mL) was added and incubated at 37° C. in darkness. Four hours later, the supernatants were discarded and 100 μL of DMSO per well were added to dissolve the formazan during 10 minutes. The absorbance was measured at 570 nm and 630 nm using a multi-well plate reader (Model VICTOR™ X4, PerkinElmer).

For each condition, the number of cells was evaluated using the following equation:

$$OD_{\lambda 570}\text{ sample} - (OD_{\lambda 630}\text{ sample} + OD_{\lambda 570}\text{ blank});$$

and the results were expressed as percentage versus control condition.

6.2 Cell Number and (Second) Cell Viability Assays Protocols

The number of cells was evaluated by crystal violet staining Cells were plated in 96-well plates and cultured with various concentrations of YL3 (1, 3, 10, 30, or 100 μmol/L). After 2-h incubation, cells were stained for 15 min with 100 μL of a 2 mg/ml crystal violet solution (in distilled water). After careful aspiration of the crystal violet solution, the plates were extensively washed with water, and air-dried prior to solubilisation of the bound dye with 100 μL of DMSO for 10 min in darkness. The absorbance was measured at 570 nm and 630 nm using a multi-well plate reader (Model VICTOR™ X4, PerkinElmer).

For each condition, the number of cells was evaluated using the following equation:

$$OD_{\lambda 570}\text{ sample} - (OD_{\lambda 630}\text{ sample} + OD_{\lambda 570}\text{ blank});$$

and the results were expressed as percentage versus control condition.

6.3 Vascular Reactivity Studies Protocol

Potassium chloride (KCl), Acetylcholine (Ach), and Catalase (CAT) were obtained from Sigma-Aldrich and dissolved in distilled water to make stock solutions.

Male 15 weeks-old C57Bl/6J mice (Elevage Janvier, Le Genest-St-Isle, France) were used in these experiments. Mice were anesthetized with Ketamin/xylasin injection before sacrificing them and aorta arteries were removed and mounted onto wire myograph. Briefly, vessels were mounted on two 40 mm stainless steel wires in the jaws of a multi wire myograph system (Model 610M, Danish Myo Technology A/S, Aarhus, Denmark) and the myograph baths filled with physiological saline solution (PSS) with the following composition: 130 mM NaCl, 4.5 mM KCl, 1.05 mM $MgSO_4$, 20.2 mM $NaHCO_3$, 1.35 mM $CaCl_2$, 0.35 mM $KH_2PO_4$ and 11 mM glucose. PSS was heated to 37° C. and bubbled with 95% $O_2$/5% $CO_2$ to maintain a physiological pH of 7.4. Length-tension characteristics were obtained via the myograph software (Myodaq 2.01) and on the basis of these, aorta arteries were loaded to a tension equivalent to an in vivo pressure. The vessels were then left to equilibrate under these conditions for 1 h, after which they were stimulated with 50 mmol/l KCl and a concentration-response curve was constructed by a single dose of Ach (10 μM). Then vessels were washed and pre-incubated in presence or absence of catalase 500 U/ml during 20 minutes. A new contraction curve with 50 mmol/l KCl was performed and once a maximal contraction had been achieved, a single dose of YL3 (10 μM) was added and changes in tension recorded during 2 hours. At the end, a concentration-response curve was constructed by a single dose of Ach (10 μM). Ach relaxation responses were expressed as percentage relaxation to KCl contraction.

All experiments were performed in the presence of indomethacin (10 μmol/L).

Results are expressed as means±SEM and n reflects the number of animals.

Significant differences between groups were calculated by ANOVA followed by a Bonferroni test. $p<0.05$ was considered significant.

6.4 Results:

In the presence of catalase, cycloxygenase inhibitor and a high potassium extra cell concentration, the relaxation of mice aortic rings, induced by muscarinic receptors stimulation uniquely rest on NO produced by endothelial cells. In this situation, YL3 inhibits the relaxation induced by acetylcholine, as what is hoped for an eNOS inhibitor (FIG. 7). YL3 can not modify the viability of endothelial cells (HUVEC). A weak inhibition of mitochondrial metabolism of smooth muscle cells can be detected.

EXAMPLE 7

Angiogenesis Assays 7.1: Protocol:

To assess in vitro the angiogenic process, an assay of endothelial network formation (eg, plating of endothelial cell (EC) on Matrigel) was used as previously reported (14,20). EC reorganization in capillary-like structures was observed using an inverted phase contrast microscope and the length of the endothelial network quantified by analysis of images randomly captured by a video-camera system. Because inevitable interlot differences in the composition of growth-factor deprived Matrigel (eg, in the basal proangiogenic capability of Matrigel), the extent of the endothelial network in the different conditions tested was always compared within a same set of experiments and relative values were used for interassay comparisons.

Human Umbilical Vein Endothelial Cells (HUVECs) at passage 3-5 were used in these experiments.

Results are expressed as endothelial network percentage±SEM versus control condition and n reflects the number of experiments.

Significant differences between groups were calculated by ANOVA followed by a Bonferroni test.

P<0.05 was considered significant.

7.2 Results:

Significant differences between groups showed the anti-angiogenic effect of YL3 on an angiogenesis assay (FIG. 8).

EXAMPLE 8

Imaging Study of NS1 and Co-localization with Sub-cellular Organelle Markers and a Monoclonal Antibody Against eNOS NS1 imaging in endothelial cells: The fluorescence selectivity of NS1 for constitutive NOS prompted us to test if NS1 would specifically highlight eNOS in living cells. A rapid uptake of NS1 (10 min maximum in incubation) by living human umbilical vein endothelial cells (HUVECs) was easily monitored upon excitation in the near infra red, showing the suitability of NS1 for 2-PE fluorescence studies of living cells (FIG. 9). The bound NS1 showed intense fluorescence in the cytoplasm, especially in the perinuclear region and—to a lesser extent—at the cell membrane (FIGS. 9a, 11a,d). The dots at the cell membranes were prominent at high cell confluence, in agreement with the role of eNOS in the maintenance of tight cell to cell junctions. The sub-cellular localization of NS1 within organelles was then further investigated by co-localization experiments. NS1 mainly co-localized with the Golgi apparatus identified by Golgi-specific tracker (FIG. 9e-h). NS1 did not co-localize with the endoplasmic reticulum, cell nucleus or mitochondria while only partial co-localization was observed with early endosome (EEA1) (FIG. 10). The two main locations of NS1 (Golgi and plasma membrane) are compatible with the sub-cellular localization of eNOS. Using specific immuno-staining of eNOS combined to one- (FIG. 11a-c) or two-photon (FIG. 11d-f) imaging of NS1, we observed an excellent co-localization of NS1 and eNOS, in the perinuclear region and at the plasma membrane level, showing that NS1 actually targets eNOS in HUVEC cells. Because the 2-PE process avoided cellular autofluorescence, the signal-to-noise ratio was remarkably higher using two-photon compared to one-photon imaging, as judged by the more restricted co-localization area obtained using $\lambda$ex=840 nm instead of 488 nm.

EXAMPLE 9

Effect of NS1 on Superoxide Formation by PMA-stimulated RAW 264.7 Cells

Generation of superoxide by phorbol ester-stimulated W 264.7 cells was monitored by EPR spectroscopy using spin-trapping experiments in the presence of the cyclic nitrone DEPMPO.

9.1: Protocol:

Cells were incubated for 20 minutes at 37° C. under a 5% CO2 atmosphere in 5 mL fresh DMEM medium containing 5% FCS and 10 µM phorbol 12-myristate-13-acetate (PMA, from Sigma). They were washed two fold with 5 mL PBS and 1 mL of a trypsine/EDTA mixture was added to detach the cells. Following a 7 min incubation at 37° C., cells were collected in 4 mL DMEM containing 5% FCS, centrifugated for 5 min at 900 g and 4° C. The cell pellet was resuspended in 5 mL PBS, counted, and centrifugated again for 5 min at 900 g and 4° C. The pellet was resuspended in 97 mL PBS containing 100 µM DTPA, 25 mM DEPMPO, and variable concentrations of NS1 The suspension was transferred into a gas-permeable Teflon tube and inserted into an shq001 cavity. Data accumulation was started immediately. Measurements were carried out at 21° C. in a Bruker EPR Elexsys 500 spectrometer operating at X-band frequency (9.82 GHz). The following instrument settings were used: field modulation frequency, 100 kHz; field modulation amplitude, 0.2 mT; field sweep: 12 mT; center field: 348 mT; time constant, 0.081 s; microwave power, 10 mW; scan time, 41.9 s; number of scans, 40. DEPMPO-OOH spectrum was identified by comparison with incubations performed in the presence of xanthine/xanthine oxidase. The relative amounts of DEPMPO-OOH and DEPMPO-OH adducts observed in the incubation mixtures were estimated by X-sophe software simulations (Bruker).

9.2: Result:

Incubations of PMA-stimulated RAW 264.7 cells in the presence of DEPMPO lead to the formation of the characteristic 8-line features corresponding to the DEPMPO-OOH spin-adduct (a nitroxide) and their intensity increased in a time-dependent manner. The amounts of the DEPMPO-OOH spin-adduct were reduced in a concentration-dependent manner by the addition of NS1 and an IC50 value close to 25 µM was measured.

EXAMPLE 10

Effect of NS1 on Nitrite Formation by LPS+IFN-γ Stimulated RAW 264.7 Cells

Treatment of RAW 264.7 macrophage cells by LPS and IFN-γ induces the expression of inducible NOS. Nitrite, the stable end product of NO, was quantified in culture medium using the Griess reagent.

10.1 Protocol:

Cell suspension (100 µL, 2.10+6 cells/mL) in fresh DMEM medium containing 5% FCS was distributed in a 96-well plate and 100 µL of medium containing 160 U/mL IFN-γ and 200 U/mL LPS were added to each well containing various concentrations of NS1 (introduced as 2 µL of a x 100 concentrated solution in DMSO). Control incubations contained the same amount (1%) of DMSO). Cells were incubated for 15 h at 37° C. in a 5% CO2 atmosphere and 100 µL of medium was reacted with 100 µL of 1% sulfanilamide and 100 µL of 0.1% N-(1-naphthyl)ethylenediamine (both in 0.5 M HCl). The absorbance at 540 nm was read on a 96-plate reader and the nitrite concentration was determined from a sodium nitrite standard curve processed under the same conditions.

10.2: Results:

Nitrite ion accumulated in the supernatants of LPS+IFN-γ treated RAW 264.7 cells and about 60±10 µM $NO_2^-$ were detected in supernatants of cells in the presence of 1% DMSO. This accumulation was inhibited in a concentration-dependent manner by the addition of NS1 with an IC50 value of 100±20 µM.

EXAMPLE 11

Inhibition of NO Formed by BAEC (Bovine Artery Endothelial Cells) Cells by NS1

11.1 Protocol:

BAEC (bovine artery endothelial cells) were cultured till passage 5-7. Confluent BAEC cells were incubated for one hour with or without 30 µM NS1 in their basal state or after activation with calcium ionophore A23187 at the concentration of 2 µM. The spin trap Fe(DETC) was then added to the cells to trap the NO formed and the adduct Fe(DETC)-NO was quantified by EPR spectroscopy (see method in: Gautier C. van Faassen E., Mikula I., Martasek P. and Slama-Schwok A. (2006) Biochem. Biophys. Res. Comm. 341 816-821 and Anatoly F. Vanin, Lonneke M. Bevers, Anny Slama-Schwok and Ernst E. van Faassen. (2007) Cellular and Molecular Life Sciences 96-103).

11.2 Results:

NO formed by activated BAEC cells amounted 250% that formed in their basal state. Addition of 30 µM NS1 to activated cells resulted in only 150% of NO compared to basal state. Altogether, 30 µM NS1 resulted in (60±7) % inhibition of the NO formed by untreated cells (3 independent experiments), in agreement with the expected inhibition of eNOS by NS1.

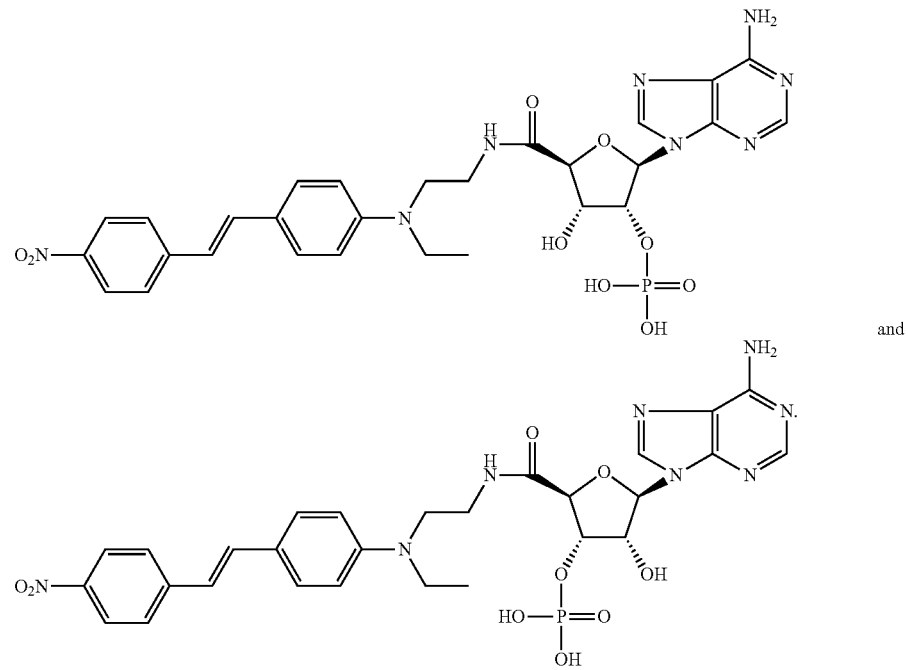

The invention claimed is:

1. Compounds of formula I:

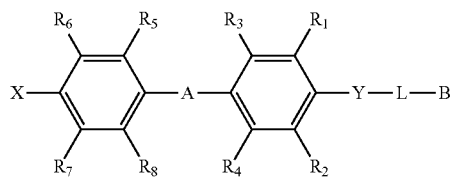

(I)

wherein:
  (i) X represents an electron acceptor group, selected from the group comprising of:
    —$NO_2$, —CN, —CHO, —COOH, —$CF_3$, —F, —CH=C(CN)$_2$, —$SO_3H$,
    $CONR_9R_{10}$ or $SO_2NR_9R_{10}$, in which $R_9$ and $R_{10}$ represent each independently of each other an hydrogen, a linear or branched ($C_1$-$C_3$) alkyl group, or an aryl group,
    $COR_9$, in which $R_9$ represents an hydrogen, a linear or branched ($C_1$-$C_3$) alkyl group, or an aryl group, and
    a tetrazolyl group,
  (ii) Y represents an electron donor group, selected from the group consisting of —$NR_{19}$—, —$OC(R_{19}R_{14})$—, and —$SC(R_{19}R_{14})$—, in which:
    $R_{19}$ is chosen from:
    a hydrogen,
    a linear ($C_1$-$C_8$) alkyl group, said alkyl group being optionally substituted by one or more group selected from: —OH group, —$NH_2$ group, —COOH group, CONH-arylCOOH group or NHCOarylCOOH group or NHCOarylsulfate group, or NHCOarylsulfonate group, wherein the aryl group is chosen from phenyl, naphtyl or biphenyl, and
    a hydrosoluble organic group, includes PEG,
    $R_{14}$ represents a hydrogen or a linear or branched ($C_1$-$C_4$) alkyl group, optionally substituted by —OH.
  (iii) A represents a bond chosen from the group consisting of:
    (a) —C≡C—, and
    (b)

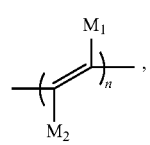

(b)

wherein:
  $M_1$ and $M_2$ represent independently of each other H, F, Cl, Br or I,
  n is an integer chosen from 1, 2, or 3,
  (iv) $R_1$, $R_2$, $R_3$, $R_4$, $R_5$, $R_6$, $R_7$ or $R_8$ are each independently selected from the group consisting of:
    —H,
    F, Cl, Br, I, and
    a linear or branched ($C_1$-$C_4$) alkyl, optionally substituted by one or more substituants chosen from:
    —OH,
    $NR_{11}R_{12}$, in which $R_{11}$ and $R_{12}$ represent each independently of each other an hydrogen or a linear or branched ($C_1$-$C_3$) alkyl group, or
    —$COOR_{11}$, in which $R_{11}$ represents hydrogen or a linear or branched ($C_1$-$C_3$) alkyl group,
    —$CONHR_{13}$ or $NHCOR_{13}$, in which $R_{13}$ represents a linear or branched ($C_1$-$C_4$) alkyl group,
  (v) L represents a spacer group selected from the group consisting of:

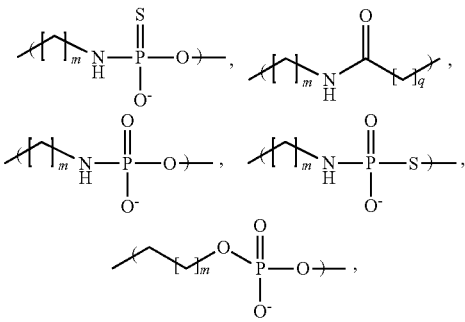

wherein m and q represent each independently of each other an integer chosen from 0 to 5, said groups being optionally substituted by one or more OH,
  (vi) B represents the following formula II:

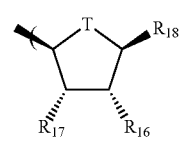

(II)

wherein:
  T represents an oxygen atom, or a sulphur atom, preferably an oxygen atom;
  $R_{16}$ and $R_{17}$ represent each independently of each other OH, $H_2PO_4$, $HSO_4$, $OPO_3(NH_4)_2$, or any salt of these phosphate or sulphate groups; and
  $R_{18}$ represents a purine-base or a pyrimidine-base, adenine, guanine, hypoxanthine, thymine, uracil or cytosine, preferably adenine,
wherein the compound of formula (I) includes racemate or isomeric forms, axial or equatorial isomeric forms, and pharmaceutically acceptable salts thereof.

2. Compound according to claim 1, of formula (Ia):

(Ia)

wherein:
R$_1$, R$_2$, R$_3$, R$_4$, R$_5$, R$_6$, R$_7$, R$_8$, X, A, L, T, R$_{16}$, R$_{17}$, R$_{18}$ R$_{19}$ are as defined above.

3. Compounds according to claim 1, of formula (Ib):

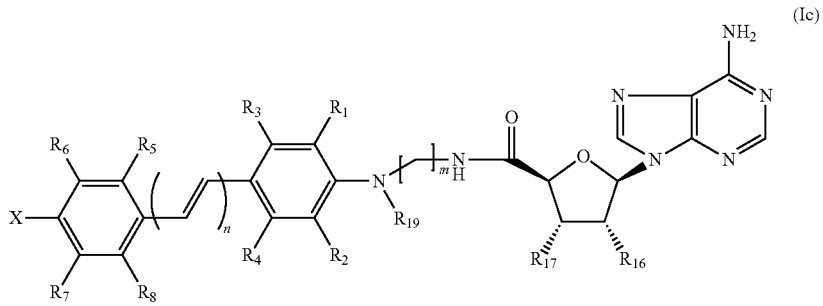

(Ib)

wherein:
R$_1$, R$_2$, R$_3$, R$_4$, R$_5$, R$_6$, R$_7$, R$_8$, X, L, n, R$_{16}$, R$_{17}$, R$_{18}$ are as defined in above.

4. Compounds according to claim 1, of formula (Ic):

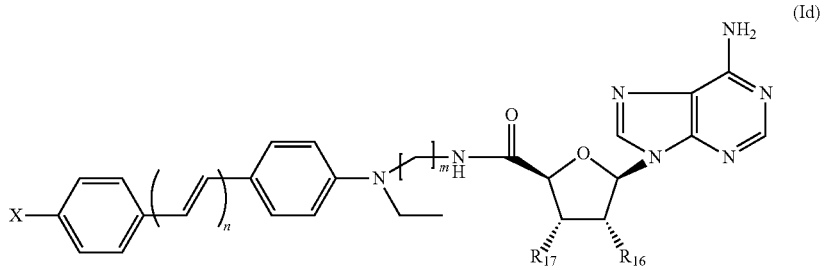

(Ic)

wherein:
R$_1$, R$_2$, R$_3$, R$_4$, R$_5$, R$_6$, R$_7$, R$_8$, X, n, m, R$_{16}$, R$_{17}$, R$_{19}$ are as defined above.

5. Compounds according to claim 1, of formula (Id):

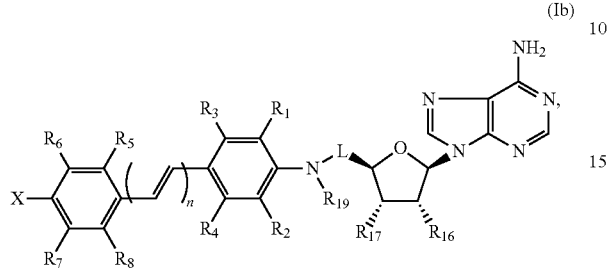

(Id)

wherein:
R$_{16}$, R$_{17}$, X, n, m are as defined above.

6. Compounds according to claim 1, characterised in that when the bond A is represented by

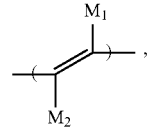

wherein M$_1$ and M$_2$ represent independently of each other H, F, Cl, Br or I, said compound is in biologically active trans form.

7. A method for treating cancers, comprising administering to a subject in need thereof an effective amount of the compound according to claim 1 as an anti-angiogenic agent in chemotherapy.

8. The method according to claim 7, wherein the cancer is a superficial cancer, in particular chosen from melanomas, upper respiratory tract cancers, and upper aero-digestive tract cancers.

9. The compound according to claim 1, wherein X represents an electron acceptor group selected from the group consisting of:

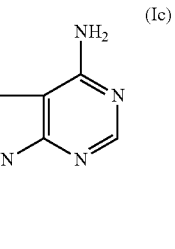

—NO₂, —CHO, —COOH, —CF₃, —F, —CH═C(CN)₂, —SO₃H,

CONR₉R₁₀ or SO₂NR₉R₁₀, in which R₉ and R₁₀ represent each independently of each other an hydrogen, a linear or branched (C₁-C₃) alkyl group, or an aryl group, COR₉, in which R₉ represents an hydrogen, a linear or branched (C₁-C₃) alkyl group, or an aryl group, and a tetrazolyl group.

10. The compound according to claim 1, wherein the compound is selected from the group consisting of